(12) United States Patent
Hirabayashi et al.

(10) Patent No.: US 6,673,547 B2
(45) Date of Patent: Jan. 6, 2004

(54) DNA ANALYSIS SYSTEM

(75) Inventors: Atsumu Hirabayashi, Kodaira (JP); Min Huang, Kodaira (JP); Yukiko Hirabayashi, Kokubunji (JP); Akihiko Okumura, Hachioji (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/941,769

(22) Filed: Aug. 30, 2001

(65) Prior Publication Data

US 2002/0127566 A1 Sep. 12, 2002

(30) Foreign Application Priority Data

Jan. 18, 2001 (JP) .......................... 2001-010357

(51) Int. Cl.$^7$ .......................... C12Q 1/68; C12P 19/34; C07H 21/00; C07H 21/02
(52) U.S. Cl. .................. 435/6; 435/91.1; 435/91.2; 536/25.3; 536/25.4; 935/77; 935/78
(58) Field of Search .................. 435/6, 91.1, 91.2; 536/25.3, 25.4; 935/77, 78

(56) References Cited

U.S. PATENT DOCUMENTS

| | | | | |
|---|---|---|---|---|
| 4,353,242 A | * | 10/1982 | Harris | 73/23.1 |
| 4,861,988 A | | 8/1989 | Henion et al. | 290/288 |
| 4,935,624 A | | 6/1990 | Henion et al. | 250/288 |
| 5,605,798 A | * | 2/1997 | Koster | 435/6 |
| 5,885,775 A | * | 3/1999 | Haff | 435/6 |

OTHER PUBLICATIONS

Daniel Little, et al., "Maldi on a Chip: Analysis of Arrays of Low–Femtomole to Subfemtomole Quantities of Synthetic Oligonucleotides and DNA Diagnostic Products Dispensed by a Piezoelectric Pipet", Analytical Chemistry, vol. 69, No. 22, Nov. 15, 1997, pps. 4540–4546.

Mark T. Krahmer, et al., "Electrospray Quadrupole Mass Spectrometry Analysis of Model Oligonucleotides and Polymerase Chain Reaction Products: Determination of Base Substitutions, Nucleotide Additions/Deletions, and Chemical Modifications", Analytical Chemistry, vol. 71, No. 14, Jul. 15, 1999, pps. 2893–2900.

Viswanatham Katta, et al., "Conformational Changes in Proteins Probed by Hydrogen–exchange Electrospray–ionization Mass Spectrometry", Rapid Communications In Mass Spectrometry, vol. 5, (1991), pps. 214–217.

Atsumu Hirabayashi, et al., "Mulltiply–charged Ion Formation by Sonic Spray", Rapid Communications in Mass Spectrometry, vol. 10, (1996), pps. 1703–1705.

* cited by examiner

Primary Examiner—Ethan Whisenant
Assistant Examiner—Arun K Chakrabarti
(74) Attorney, Agent, or Firm—Antonelli, Terry, Stout & Kraus, LLP

(57) ABSTRACT

A genome DNA analysis method and a genome DNA analysis system of the present invention generates multiply-charged ions with 5 or more electric charges by an ionization process using air atomization. Also, a mass spectrometric spectrum thereof is detected and compared with predicted mass spectrum patterns in the presence or absence of polymorphism to determine a base at a polymorphic point.

20 Claims, 15 Drawing Sheets

Fig. 5
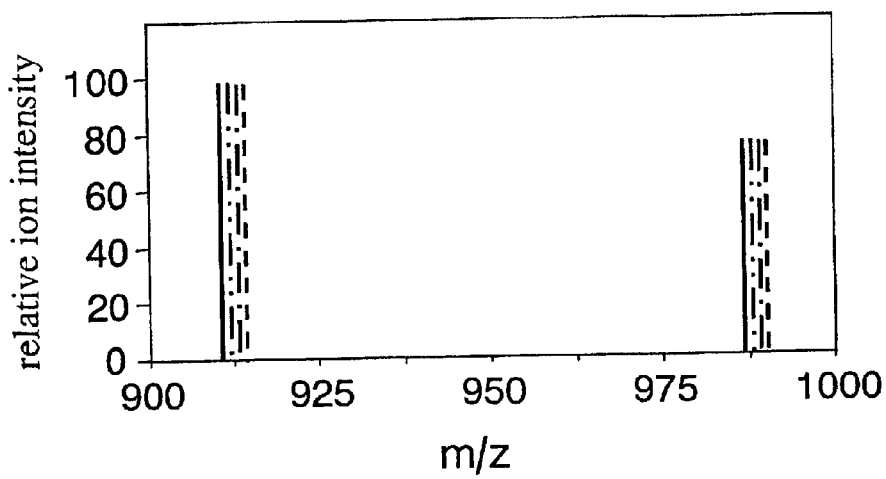
(a)
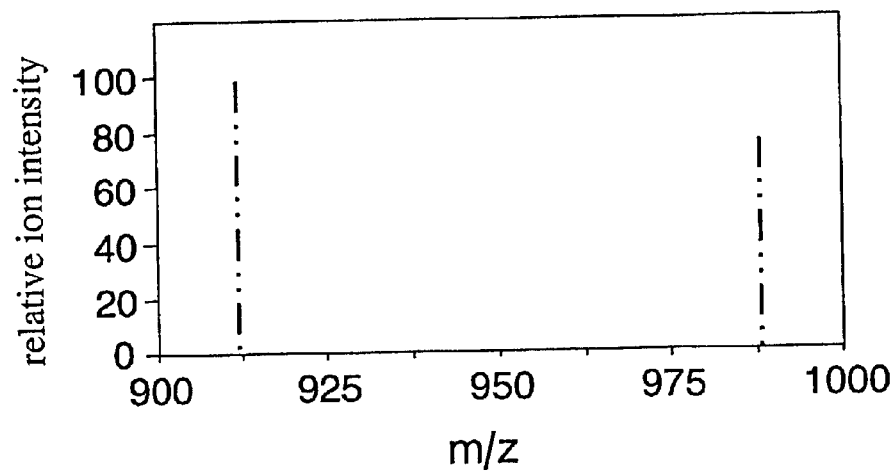
(b)
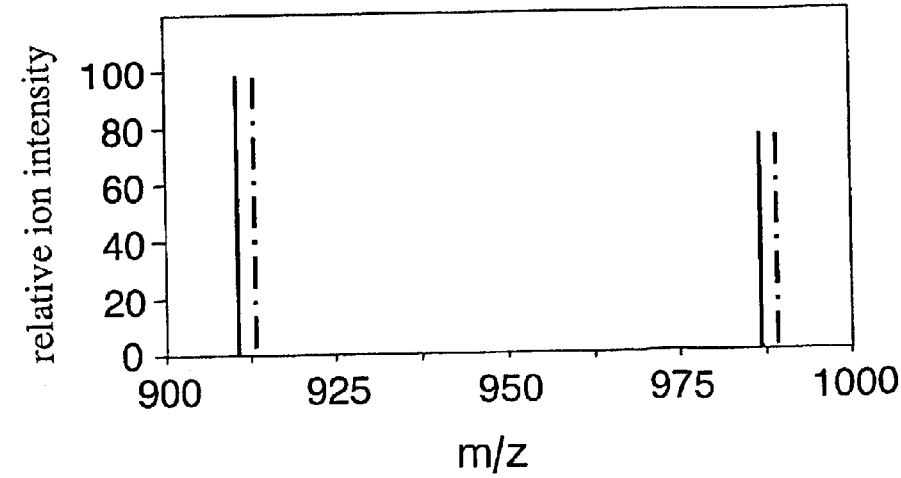
(c)

Fig. 6
(a)
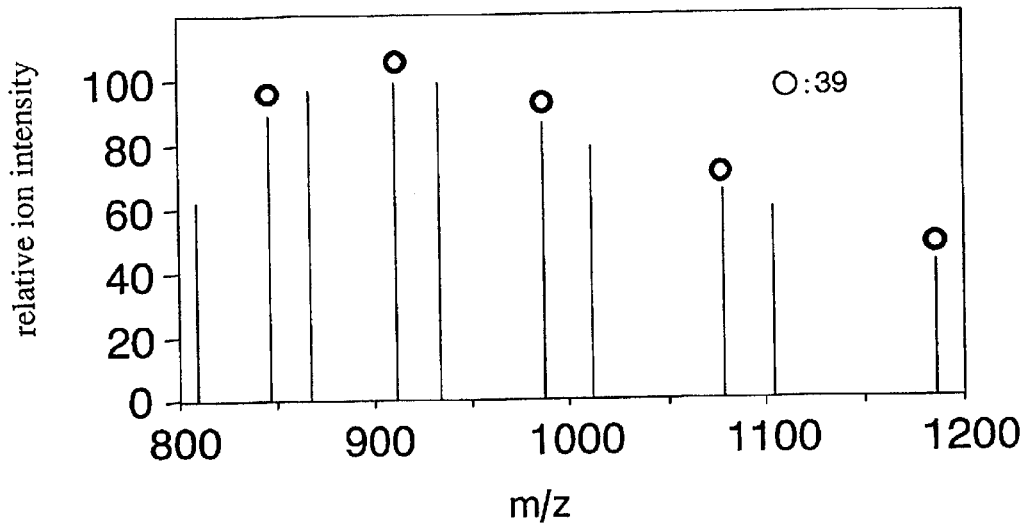
(b)
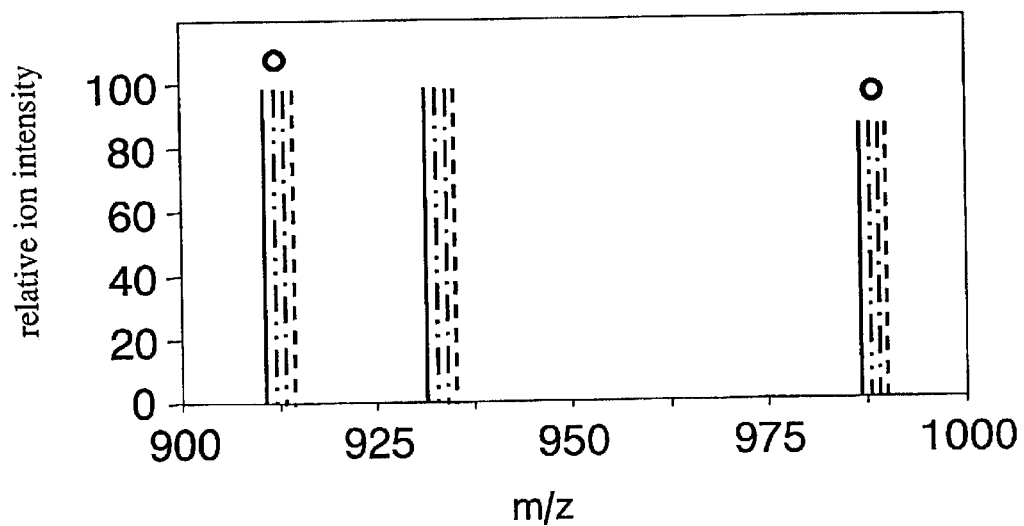

Fig. 13
status of analysis:
normal
| label number | base | notice |
|---|---|---|
| 000814104853 | A | |
| 000814104854 | A | |
| 000814104855 | A,T | |
| 000814104856 | A | |
| 000814104857 | A | |
| 000814104858 | A | |
| 000814104859 | T | |
| 000814104900 | A | |
| 000814104901 | A | |
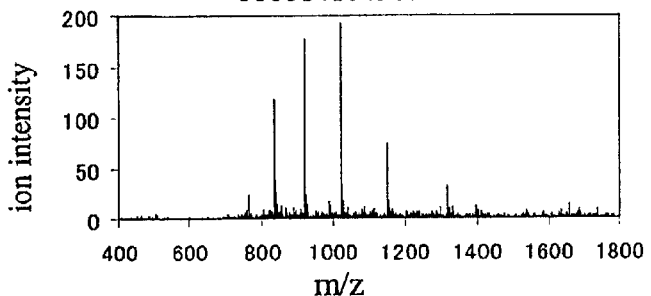
status of analysis:
emergency shutdown
| label number | base | notice |
|---|---|---|
| 000814104853 | A | |
| 000814104854 | A | |
| 000814104855 | A,T | |
| 000814104856 | A | |
| 000814104857 | A | |
| 000814104858 | A | |
| 000814104859 | T | |
| 000814104900 | ? | |
| ############ | | standard sample |
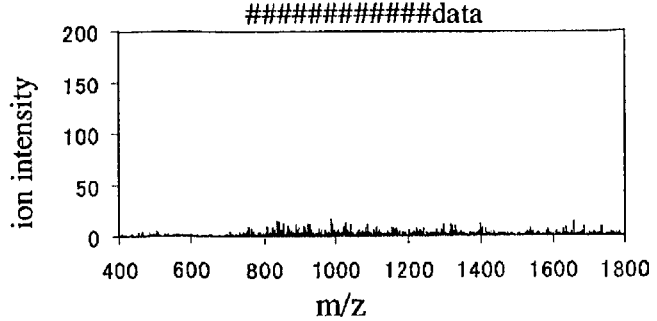

DNA ANALYSIS SYSTEM

BACKGROUND OF THE INVENTION

1. Field of the Invention

The present invention relates to measurements on biological materials, which require a high throughput. Specifically, the present invention relates to a method and system for analyzing DNA-polymorphisms in the human genome, such as single nucleotide polymorphisms (SNPs) that are single-base variations at a unique physical location among different individuals.

2. Description of the Prior Art

It is thought that there are about $10^3$ to $10^5$ of SNPs portions in the human genome. For facilitating genomic drug discovery and developing personalized medicines, there is a need to analyze those SNPs portions for many individuals. Accordingly, a high throughput of the analysis of genomic DNA has been required in the field of the related art.

A matrix-assisted laser desorption ionization time-of-flight mass spectrometer (MALDI-TOFMS) has been known in the art. It is described in publications, such as Little, D. P. et al., Analytical Chemistry, pages 4540–4546, no. 22, vol. 69, 1997. In this document, such a mass spectrometer performs analyses on genome DNA samples by applying each sample on a silicon substrate, placing the substrate in a vacuum apparatus, and detecting a mass spectrum for univalent or divalent ions.

In this mass spectrometer, there are tendencies to decrease the sensitivity of the detection thereof with respect to any ion with 10,000 or more of mass-to-charge ratio (m/z: the mass of an ion per the number of electric charges of the ion). Therefore, the mass spectrometer may be used for the analysis on a short-stranded DNA fragment with a base length of 30 bases or less.

The above measurement apparatus (MALDI-TOFMS) carries out a measurement on a DNA sample being applied on the silicon substrate and then placed in a vacuum apparatus. Alternatively, there is another apparatus that allows a measurement on a genome DNA sample being kept in a liquid state. Such an apparatus is described in the document of Krahmer, M. T. et al., Analytical Chemistry, pages 2893 to 2900, no. 14, vol. 71, 1999. In this measurement apparatus, a sample of genome DNA with several tens of bases in a liquid state is ionized by means of electrospray ionization. The mass of genome DNA is then detected by means of mass spectrography. In this case, the results are characterized in that a plurality of multiply-charged ions with 10 or more charges is mainly detected within the limits of m/z=700 to 1,400 in contrast to those obtained by the MALDI-TOFMS.

In the document of Rapid Communication in Mass Spectrometry, pages 214 to 317, vol. 5, 1991, there is described an example in which an electrospray ionization method is applied for performing the analysis on multiply-charged ions of a protein molecule. In this measurement apparatus, a mass spectrum with several peaks is caused by respective multiply-charged ions with 6 to 13 charges. The mass of protein provided as a sample to be measured can be estimated from the mass-to-charge ratio (m/z) that corresponds to the respective peak positions of the mass spectrum.

In this case, a sample being kept in a liquid state may be introduced into the measurement apparatus using the electrospray ionization method at the rate of about 1 to 7 micro-litters per minute.

In the conventional technology using the MALDI-TOFMS described above, there are some problems that need to be addressed. For example, the inside of the vacuum apparatus tends to be contaminated because the conventional process using the above MALDI-TOFMS subjects the sample to a sputtering step using a laser beam irradiation in the vacuum apparatus. If the inside of the vacuum apparatus becomes contaminated, it decreases the efficiency of converging ions to be generated. As a result, there are problems with respect to degradation in sensitivity, reproducibility, or the like. For reducing the possibility of causing any harmful influence of the contamination, there is a need to perform a complicated cleaning repeatedly at frequent intervals. In this case, however, the frequent cleaning may interrupt the continuous measurement for many hours. As a result, and thus the average throughput thereof is decreased. In the case of the MALDI-TOFMS, furthermore, ions to be detected by the mass spectrum are of only two types, monovalent and divalent, so that there is another problem that a need for re-measurement when none of two types cannot be detected.

On the other hand, another conventional technology depending on the electrospray ionization method uses a syringe pump, where multiply-charged ions are generated by performing electrospray ionization, followed by the measurement. In this case, it is possible to introduce a sample into the syringe pump continuously, but only one kind of the sample can be subjected to the measurement. If different kinds of samples are introduced into the same syringe pump for the measurement, the remainder of one sample in the syringe affects on the measurement of another sample. Therefore, it causes the lower measurement accuracy. In addition, the replacement of the syringe pump with another one is a time-consuming job, so that each of successive measurements on many samples with high throughputs requires a great deal of time and much effort.

As described above, therefore, demands for a high throughput have not been satisfied by the conventional genome DNA analysis system.

SUMMARY OF THE INVENTION

It is an object of the present invention is to provide a method for the analysis of DNA polymorphism, which allows a long-duration measurement with a high throughput and achieves a stable measurement even though the concentration of a sample is low. It is another object of the present invention is to provide a system for DNA analysis, which allows a long-duration measurement with high throughput and achieves a stable measurement even though the concentration of a sample is low.

For solving the problems associated with the conventional technologies described above, a novel DNA analysis system comprises an ionization part that employs an air atomization method such as an electrospray ionization or sonic spray ionization for allowing a continuous introduction of samples into the ionization part, to attain a high-through put measurement. If the samples are successively introduced into the ionization part, it is difficult to neglect an adsorption of the sample on a sample capillary, an ion source, or the like. Any conditioning step may be performed to avoid the undesired influences of the adsorbed samples from a mass spectrum to be analyzed so that the analysis is carried out without decreasing its accuracy.

Furthermore, the present inventors improve the analytic accuracy of the system by performing a sample measurement and a data analysis using the fact that multiply-charged ions with 5 or more charges when a genomic DNA sample is ionized by an ionization process using an air atomization.

Furthermore, the present inventors provide a genome DNA analysis system that allows a speedy backup when any emergency occurs in the system. Such a backup can be attained by comprising means for holding a standard sample, a plurality of measurement systems, display means for displaying the results of analysis, communication means to make a communication with a system administrator, and so on.

The above and the other objects of the present invention will be attained by the following configurations of the DNA analysis system.

(1) In the first aspect of the present invention, a DNA analysis system for analyzing DNA polymorphism, includes: ionization means for generating plural kinds of multiply-charged ions of a test DNA fragment, where each of them has five or more charges; mass spectrometric means for performing a mass spectrometry on the multiply-charged ion formed by the ionization means; analyzing-result prediction means that predicts a mass spectrum pattern from the mass spectrometric means in each of two cases, where one is that the test DNA fragment is polymorphic and the other is that the test DNA fragment is not polymorphic, based on both information about the test DNA fragment and information about a polymorphism point; comparative processing means for comparing a plurality of the mass spectrum patterns predicted by the analyzing-result prediction means with the analyzed results of the test DNA fragment analyzed by the mass spectrometric means to determine a nucleic acid base on the polymorphism point.

The information about the test DNA fragment includes the number of each of four different nucleic acid bases (i.e., adenine, thymine, guanine, and cytosine) that make up the test DNA fragment.

(2) In the DNA analysis system as set forth in the item (1), the analyzing-result prediction means predicts a mass-to-charge ratio (m/z; m is an ion mass, z is the number of electric charges) of the plural kinds of multi-charged ions in each of two cases, where one is that the test DNA fragment is polymorphic and the other is that the test DNA fragment is not polymorphic.

(3) In the DNA analysis system as set forth in the item (1), the analyzing-result prediction means predicts a mass-to-charge ratio (m/z; m is an ion mass, z is the number of electric charges) of the plural kinds of multi-charged ions and distribution of ion intensities in each of two cases, where one is that the test DNA fragment is polymorphic and the other is that the test DNA fragment is not polymorphic.

(4) In the DNA analysis system as set forth in the item (1), the DNA analysis system further includes: sampling means for supplying a sample including test DNA fragments to the ionization means at fixed intervals; and detecting-output analysis means for subtracting a mass spectrum obtained as an analyzing result with respect to a sample previously measured and modified by weight from a mass spectrum obtained as a detecting-output of the mass spectrometric means, wherein the mass spectrum processed by the detecting-output analysis means is provided as an analyzing result with respect of the test DNA fragment in the sample.

(5) In the DNA analysis system as set forth in the item (1), the ionization means generates multiply-charged ions of the test DNA fragment by the ionization means using an air atomization.

(6) In the DNA analysis system as set forth in the item (1), a nucleic acid base of a single nucleotide polymorphism point in the test DNA fragment is specified.

(7) In the DNA analysis system as set forth in the item (4), the DNA analysis system further includes: a display means for displaying an occurrence of an emergency when a maximum ion intensity detected by the mass spectrometric means is smaller than a predetermined threshold.

(8) In the DNA analysis system as set forth in the item (7), the DNA analysis system further includes: communication means for sending information about the occurrence of an emergency to a system administrator.

(9) In the DNA analysis system as set forth in the item (4), the sampling means introduces a standard sample into the ionization means when a maximum ion intensity of the mass spectrum detected by the mass spectrometric means is smaller than a predetermined threshold.

(10) In the DNA analysis system as set forth in the item (9), when a maximum ion intensity of a mass spectrum of the standard sample detected by the mass spectrometric means is equal to or higher than the threshold, the sample where the maximum ion intensity of the mass spectrum is detected as one smaller than the threshold is re-supplied to the ionization means by the sampling means.

(11) In the DNA analysis system as set forth in the item (9), the DNA analysis system further includes: a plurality of measurement systems, where each of the measurement systems comprises the sampling means, the ionization means, and the mass spectrometric means, when a maximum ion intensity of a mass spectrum of the standard sample detected by mass spectrometric means in one measurement system of the plurality of measurement systems is smaller than the threshold, the sample where a maximum ion intensity is detected as one smaller than the threshold at the one measurement system is transmitted to sampling means of another measurement system except the one measurement system.

(12) In the DNA analysis system as set forth in the item (9), the DNA analysis system further includes: a plurality of measurement systems, where each of the measurement systems comprises the sampling means, the ionization means, and the mass spectrometric means, wherein when a maximum ion intensity of a mass spectrum of the standard sample detected by mass spectrometric means in one measurement system of the plurality of measurement systems is smaller than the threshold, a sample intended to be measured by the one measurement system is sent to sampling means of another measurement system except the one measurement system.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIGS. 5A, 5B, and 5C illustrate predicted mass spectrum patterns for the genome DNA samples;

FIGS. 6A and 6B illustrate predicted mass spectrum patterns for the multiplexed samples:

FIG. 13 is a schematic diagram that illustrates two screens of the display means, which are displayed at the normal and emergency states, respectively;

DETAILED DESCRIPTION OF THE PREFERRED EMBODIMENTS

Preferred embodiments of the present invention will now be described with reference to the accompanying drawings.

[First Embodiment]

Figure 1:
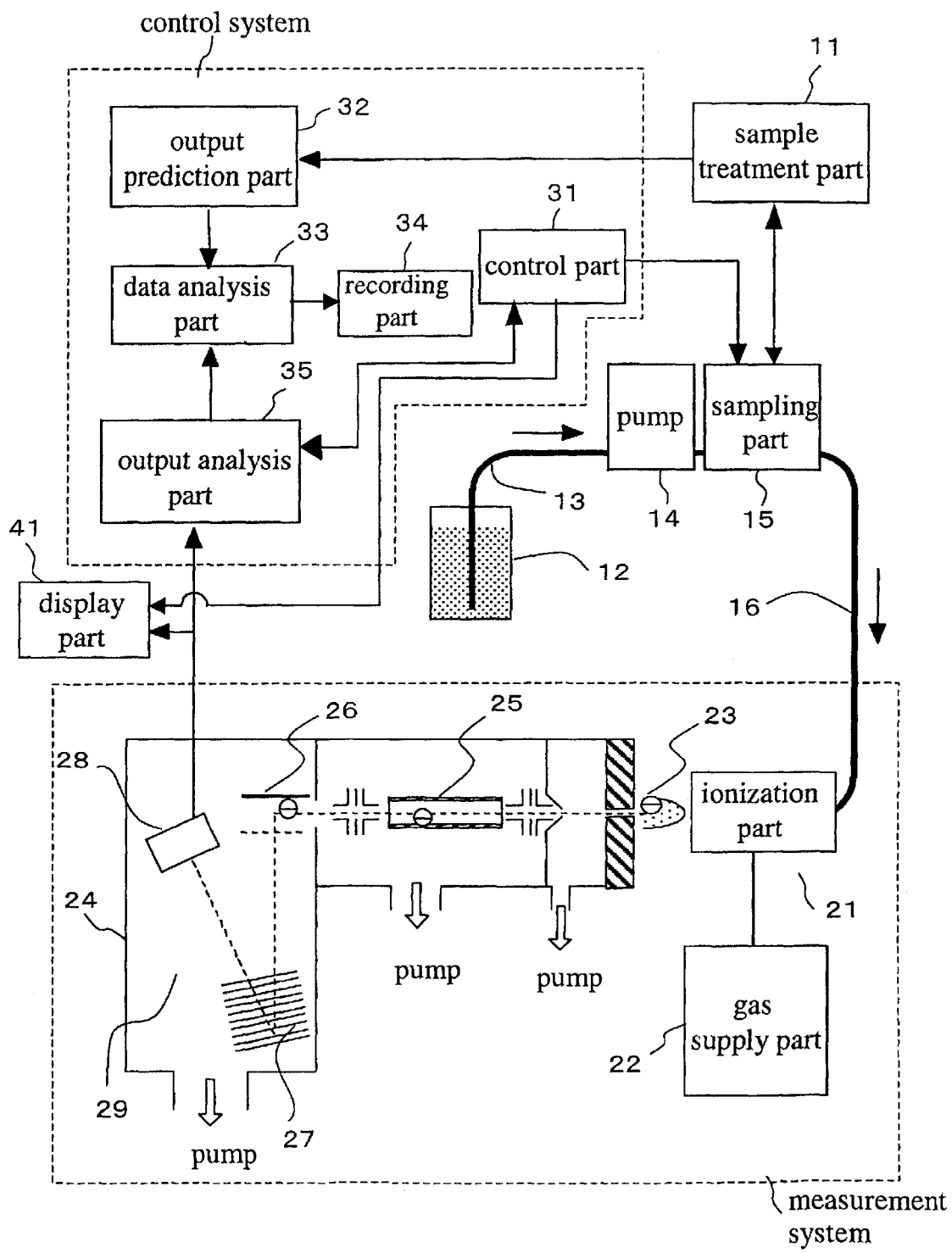
FIG. 1 is a schematic diagram that illustrates a genome DNA analysis system as a first embodiment of the present invention.

FIG. 1 is a schematic diagram that illustrates a genome DNA analysis system as one of preferred embodiments of the present invention. The genome DNA analysis system mainly includes three structural assemblies: a sample-preparation system, a measurement system, and a control system. The sample preparation system includes a sample treatment part 11 for preparing a sample, a container 12 in which a cleaning fluid is filled, a pump 14, and a sampling part 15. A sample prepared by the sample preparation system is transferred to the measurement system through the sampling part 15. The measurement system includes an ionization part 21 having a gas-supply part 22, and a mass spectrometric part 24 that carries out an analysis of multiply-charged ions 23 generated from the ionization part 21. Furthermore, the control system includes: an output prediction part 32 that predicts the results to be obtained from the analysis based on the sample information transmitted from the sample treatment part 11; an output analysis part 35 that analyzes an output from the mass spectrometric part 24 of the measurement system; a data analysis part 33 that generates the results of the sample analysis by performing a comparison between a predicted output from the output prediction part 32 and an actual output from the output analysis part 35; a recording part 34 that makes a record of the analyzing results from the data analysis part 33; and a control part 31 that controls the sampling part 15 of the sample preparation system and the output analysis part 35. Furthermore, as shown in FIG. 1, a display part 41 may be provided on the genome DNA analysis system. The display part 41 displays any information on its screen. The information includes the current analyzing status of the system (i.e., the information for defining whether the system functions normally or abnormally) and the latest analyzing results that include a mass spectrum.

A liquid sample contains various kinds of DNA fragments prepared by the sample treatment part 11. The liquid sample is kept in a sample-retaining vessel such as a 384-hole microtiter plate. On the other hand, a cleaning fluid is stored in the container 12 and is then passed into the sampling part 15 through a capillary tube 13 at a predetermined flow rate. In the sampling part 15, the sample-retaining vessel is transferred from the sample treatment part 11 into position. A sampling operation is then initiated by a control signal from the control unit 31. The sample may be introduced from the sampling part 15 into the ionization part 21 by passing the sample along the capillary tube 16 at a predetermined time period of, for example once per five seconds. Therefore, the sample can be introduced into the ionization part 21 at a predetermined time period T, while the cleaning fluid is introduced into the ionization part 21 during the remainder of the time period. Typically, the sample may be introduced into the ionization part 21 for one second and subsequently the cleaning fluid is introduced for 4 seconds. These steps may be repeated in cycles.

Next, the measurement system of the genome DNA analysis system will be described. The ionization part 21 adopts a sonic spray ionization method using a high-speed gas stream at a speed close to that of sound or an electrospray ionization method concurrently using a gas stream. The details of these ionization methods are described in Rapid Communication in Mass Spectrometry, pages 1703 to 1705, vol. 10, 1996 and the U.S. Pat. Nos. 4,861,988 and 4,935,624. The liquid sample to be introduced into the tube 16 in the sampling part 15 is further introduced into a capillary tube in the ionization part 21. Subsequently, the liquid sample is sprayed as a fine mist of small droplets from the end of the capillary by a gas stream formed on the outer periphery of the capillary. At the end of the capillary, the application of an electric field allows the dissociation of electric charges of molecular components contained in the liquid sample, so that charged droplets are generated by means of air atomization. As the charged droplet evaporates rapidly, multiply-charged ions can be efficiently generated in gaseous form.

The gaseous ions generated almost under the atmospheric pressure passes through a differential pumping region from a pore and is then introduced into an ion guide 25. In FIG. 1, a broken line represents a central track of a beam of ions. The beam of ions is cooled while passing through the ion guide 25 using multi-poles. Subsequently, the beam of ions is transferred to a high vacuum region 29 and is then subjected to a mass spectrometric analysis using a time-of-flight mass spectrometer (TOFMAS). In other words, the beam of ions is accelerated downward through the application of a high-voltage pulse on an electrode 26. Furthermore, the ion track, i.e., a path along which the beam of ions moves, is reflected by a reflector 27 and turned to a detector 28. Subsequently, the beam of ions arrives at the detector 28. In the time-of-flight mass spectrometer (TOFMAS), the beam of ions being accelerated in a pulse mode flies at a predetermined speed on the basis of its mass. Thus, a time of flight for which the ion flies over the predetermined distance can be determined by the mass of each ion. The reflector 27 may be used for correcting an energy distribution of the ion and also for the size reduction of the system.

Each sample to be prepared in the sample treatment part 11 has its own individual label number. The sample treatment part 11 links such a label number with the information about a predicted SNP portion, followed by sending to the output prediction part 32. In the output prediction part 32, a predicted pattern of a mass spectrum (i.e., a prediction of the relative intensity distribution of the mass spectrum) is calculated. The results of such a calculation are transmitted to the data analysis part 33. The control part 31 sends out a sampling start signal to the sampling part 15. Simultaneously, the control part 31 sends out the label number to the output analysis part 35 so as to link an output of the detector 28 in the mass spectrometric part 24 with the label number of the sample. The output subjected to the output analysis in the output analysis part 35 is transmitted to the data analysis part 33. Among the predicted mass spectrum patterns sent from the output prediction part 32, a prediction having the highest level of matching score (homology) is defined. Then, the results are sent to the recording part 34 and stored together with the label number on a recording medium.

In the present embodiment, as described above, the ionization part using the sonic spray method is used. A nitrogen gas is introduced from the gas supply part 22 to the ionization part 21, so that several kinds of gaseous multiply-charged ions 23 derived from the sample are generated from the liquid sample by using the high-speed gas stream formed near the end of the tube 16. The resulting gaseous multiply-charged ions are introduced into a vacuum system and subjected to a mass spectroscopic analysis in the mass spectrometric part 24. If the number of charges of the ion is an integral number close to a numeric value obtained by multiplying a base length of DNA portion by a factor of one-third (⅓), there is a tendency that an ion intensity is detected more strongly. Among the predicted mass spectrum patterns sent from the output prediction part 35, a prediction having the highest level of matching score (homology) is defined. Then, the results are sent to the recording part 34 and stored on a recording medium.

Similar results may be obtained by the electrospray ionization method. In this case, however, it is required to prevent the generation of a corona discharge. Thus, the atmosphere for generating ions may be limited to a gas having a high electron affinity, such as carbon dioxide ($CO_2$) gas. In addition, if the flow rate of gas to be used for the atomization is smaller than the predetermined one, there may be cases where the reproductivity of ion generation is decreased due to the influence of the contamination around the ionization part.

In the present embodiment, a time-of-flight mass spectrometer is used as a mass spectrometric part 24, but not limited thereto. Any mass spectrometer may be used, such as a quadrupole ion trap mass spectrometer, a quadrupole mass spectrometer, or Fourier-transform ion cyclotron resonance mass spectrometry. The resulting mass spectrum may be displayed on a screen of the display means such as an oscilloscope.

In the output analysis part 35, the sample introduced in the sampling part 15 is associated with an output from the detector 28. At this time, the processing represented by the following equation (1) is performed on the detected intensities of the mass spectrum to avoid any influence of the remaining part of the sample in the capillary tube 16 or the ionization part 21.

$$S(i) = I(i) - \sum_{n=1}^{m} w(n) I(i-n) \quad (1)$$

In the equation, $S(i)$ denotes the result of the output-analysis of the sample introduced at i-th, obtained from the output analysis part 35; $I(i)$ denotes an output from the detector 28 of the mass spectrometric part 24 to the output analysis part 35 with respect to a sample introduced at i-th in the order of samples to be measured; $w(n)$ denotes an attribute that represents a degree of the influence (interference) of a sample introduced at (i−n)th in the order of the samples against a measurement value of the sample introduced at ith, which is obtained by actual measurement. For example, if n=0, then $w(0)=1$; and m denotes a predetermined natural number. The above equation means that the influences of the remainder of the measurement sample introduced at (i−m)th in the order of the samples is removed from the output $I(i)$ of the detector 28.

A factor $w(n)$ can be defined by measuring that the changes in the ion intensities over time detected by the detector 28. If a sample is once introduced into the flow of a cleaning fluid, then the detector 28 of the mass spectrometric part 24 detects the changes in ion intensities of the sample over time. In this case, the ion intensity steeply rises at first and then gradually decreases over time as the genome DNA sample being absorbed on the inner surface of the capillary tube 16 becomes removed and dispersed therefrom. The $w(n)$ can be determined by measuring a relative ion intensity after the time "T×n" from the time at which the maximum ion intensity is observed. In other words, if the maximum ion intensity is 1 (one), then $w(1)$ is determined from the ion intensity measured at the time after T from the time at which the maximum ion intensity is measured and also the ion intensity measured at the time after 2T is determined from $w(2)$.

In the actual measurement, the samples that contain genome DNA are intermittently infused into the capillary tube 16 at predetermined intervals (T). In this case, however, the cleaning fluid is circulated in the tube 16. If the time T is more than several minutes, the factor $w(1)$ is so small to be almost negligible. If the time T becomes small, for example in the case of T=4 seconds, then the factor $w(1)$ becomes considerably large. It means that the contamination of the sample arises. Therefore, the processing such as the one indicated by the equation (1) is required.

Figure 2:
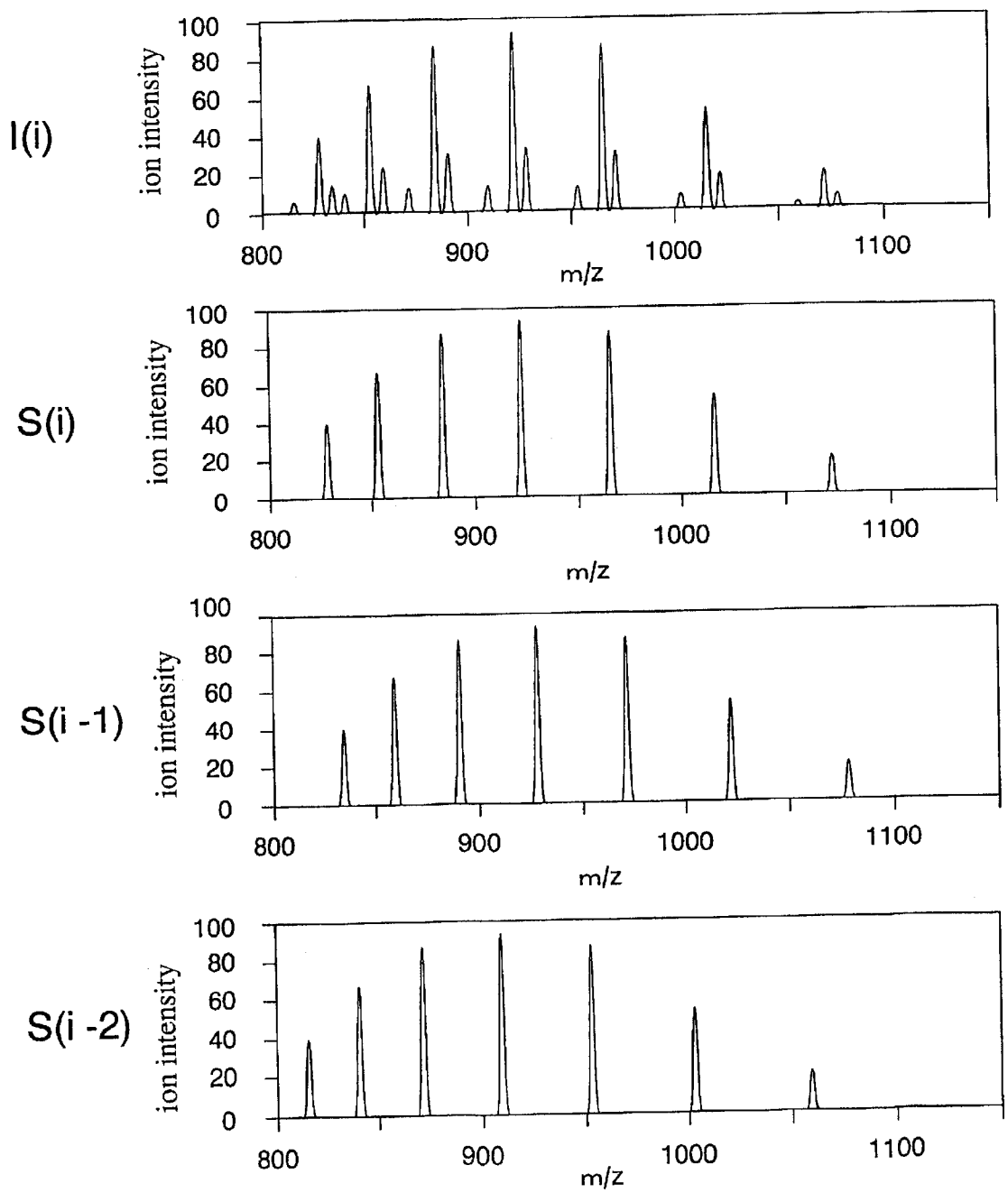
FIG. 2 is a graphical representation that illustrates charts of mass spectra of outputs I(i), S(i), S(i−1), and S(i−2)
Figure 3:
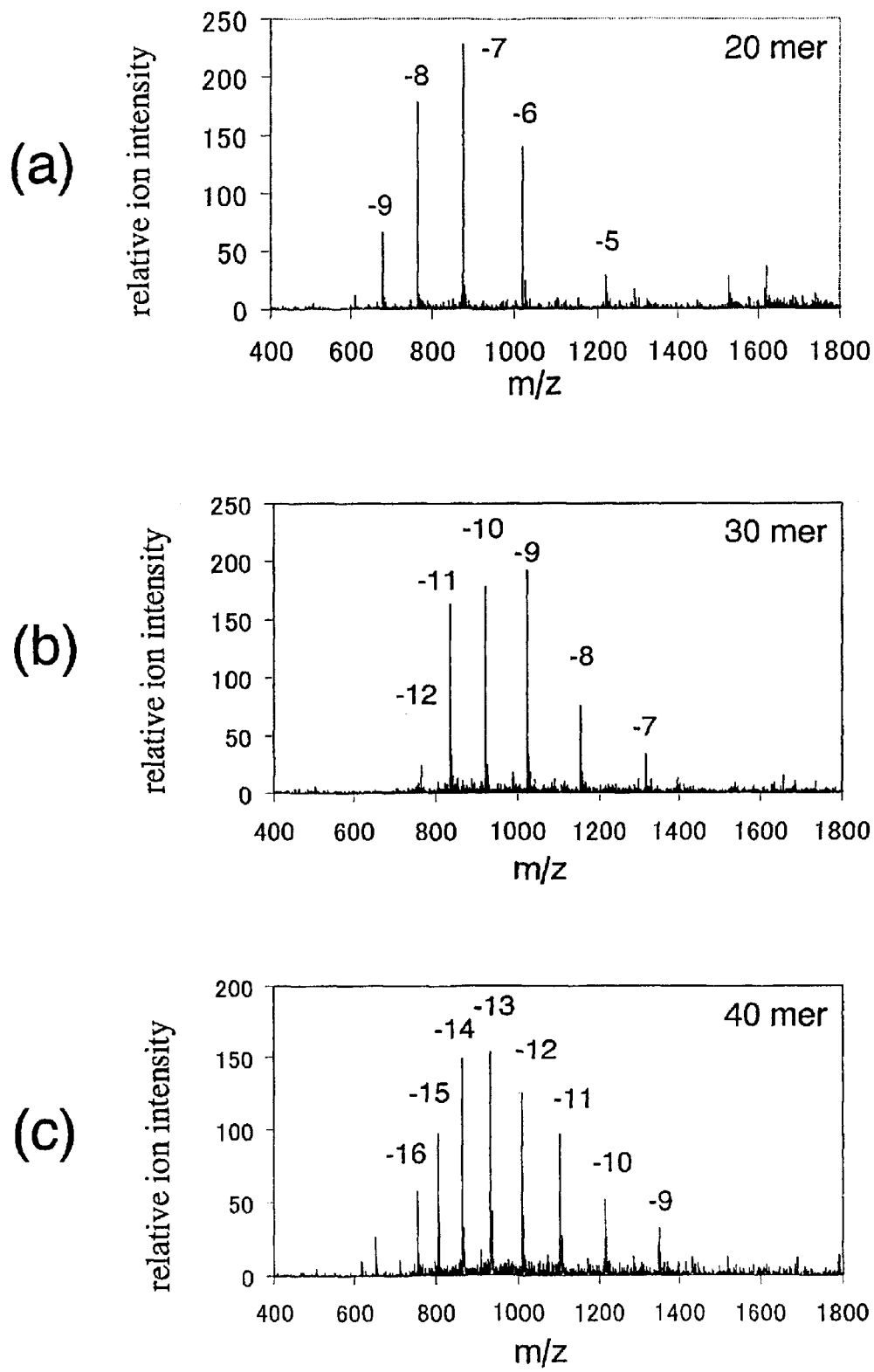
FIGS. 3A, 3B, and 3C are charts of examples of mass spectra obtained by the genome DNA analysis system of the present invention.

FIG. 2 shows charts of mass spectra that illustrate an output $I(i)$ from the detector 28 of the mass spectrometric part 24, and outputs $S(i)$, $S(i-1)$, and $S(i-2)$ from the output analysis part 35. In this case, the factor $w(n)$ is input in the output analysis part 35 in advance. In the example shown in the figure, the influences of the sample $S(i-1)$ measured by the immediately preceding measurement and the influences of the sample $S(i-2)$ measured by the measurement preceding the above measurement remarkably appear on the actual output $I(i)$ from the detector 28. Furthermore, the degrees of these influences are more increased when the sample is subjected to the more recent measurement. Therefore, the measurement value $S(i)$ can be obtained only for the i-th sample by performing a weighting and subtracting $I(i-1)$ and $I(i-2)$ from the output $I(1)$ of the detector 28 of the mass spectrometric part 24. FIG. 3 shows an example of actual data obtained by the genome DNA analysis system of the present invention. FIGS. 3A, 3B, and 3C represent the examples of the output results (mass spectra) when the samples with genome DNA of 20 base length, 30 base length, and 40 base length are measured. The horizontal axis of the graph represents the value of mass-to-charge ratio (m/z) obtained by dividing the mass m of ion with the number z of charges, and the vertical axis thereof represents a relative ion intensity.

Each of the resulting mass spectra mainly includes three or more kinds of multiply-charged ions with five or more charges, so that it is characterized in that dissociated fragment ions are hardly formed. In the case of the analysis of SNPs, the base length of a probe primer to be used for the PCR amplification of a base sequence that contains SNPs may be 15 or more in general. The genome DNA to be provided as a measurement target includes a SNPs portion in its probe region, so that the base length of the genome DNA sample becomes 16 or more. In the ionization method using an air atomization, there is a tendency that an ion intensity of the charge represented by the natural number which almost corresponds to a value obtained by dividing the base length by three. In this case, therefore, the main ion to be detected becomes that of 5 or more charges.

In the input part, a base sequence of genome DNA to be a target of the measurement and the number of adenines, guanines, cytosines, and thymines are entered in the input part. In this case, the possible base of polymorphism may be also entered. Furthermore, in case of polymorphism if the number of other bases to be substituted is one or two, there is no need to assume three types of polymorphism. Therefore, any substituted basis can be also entered. Based on the information, the output prediction part calculates the output results to be predicted by means of the following equations.

$$m = 313.21 N_A + 304.19 N_T + 329.21 N_G + 289.18 N_C - 60.96 \quad (2)$$

$$N = N_A + N_T + N_G + N_C \quad (3)$$

wherein m represents the mass number of ion; $N_A$, $N_T$, $N_G$, and $N_C$ represent the numbers for four kinds of the bases (i.e., adenine, thymine, guanine, and cytocine) that make up the genome DNA, respectively; and N represents a base length. In the case where the polymorphic part is adenine, the genome DNAs to be detected can be, for example, a series of bases that are not polymorphic, three series of bases that are polymorphic and in which $N_A$ decreases only 1 (one) and each of $N_T$, $N_G$, and $N_C$ is incremented by 1 (one) in principle. In many cases, as described above, it may be sufficient to assume only one or two series of polymorphism. The homo-type has either of major or minor types, so that from two to four types are assumed. That is, two types (one major type and one minor type) and four types (one major type and any of three possible minor types). In case of the hetero-type, two kinds of genome DNA, major and minor, are present in the same person, so that the output results are overlapped together almost at the same intensities. In this case, the output results can be assumed from one (a combination of a major and a minor) to three types (any of three possible combinations of majors and minors). As a result, from three combinations (two homo-types and one hetero-type) to seven combinations (four homo-types and three hetero-types) in total can be estimated.

There is another way without considering any hetero-types in the output results to be predicted. In a matching score search, in this case, the largest resulting peak intensity and the second largest resulting peak intensity are outputted to determine whether they are heterogeneous or not. If the second result is extremely low compared with the first one, they are defined as a homo-type and the first result is outputted. If the first result and the second result are almost the same, they are defined as a hetero-type.

According to the genome DNA analysis system of the present invention, as described above, an ion shows a high ion intensity when the number of electric charges z of the ion to be generated is an integer number that approximates to a number obtained by dividing the base length by three. Therefore, three different numbers around such an integer number in total are considered. For example, if N equals 30 (N=30), then N/3 equals 10. Thus, at least z=9, 10, and 11 should be considered. Consequently, the value of m/z for a major peak intended to be detected can be defined as three to seven different values.

Figure 4:
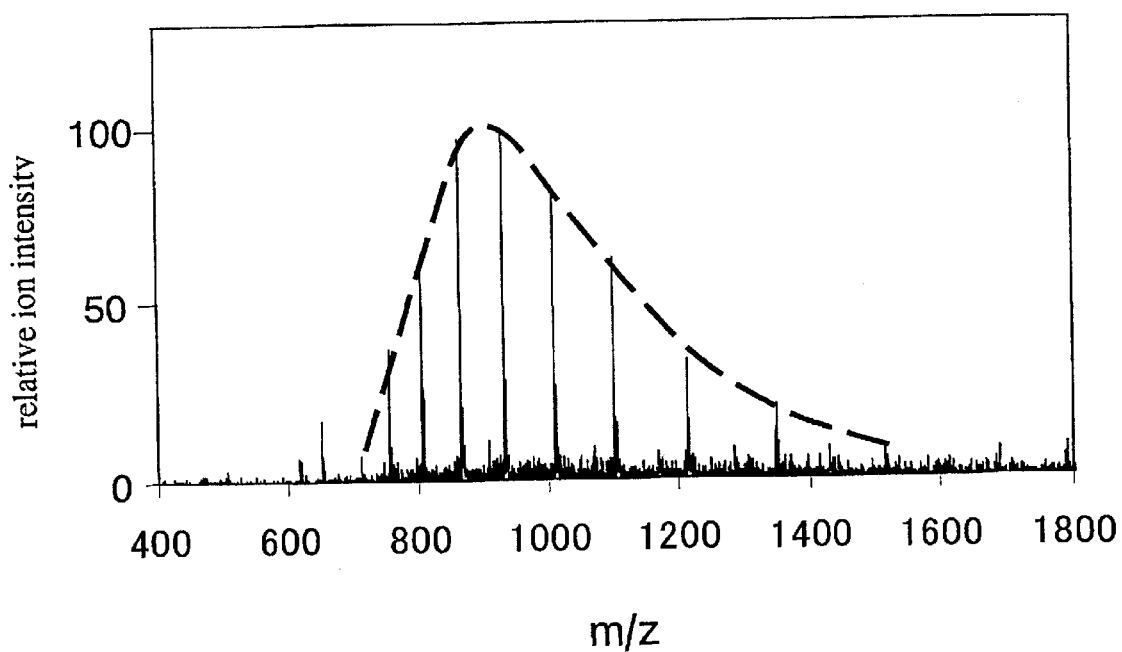
FIG. 4 is a graphical representation that illustrates a distribution of ion intensities (distribution profile of peaks)

FIG. 4 indicates a typical example showing an ion intensity distribution (a distribution profile of peaks) of a mass spectrum to be measured. A relative ion intensity corresponding to "z" or "m/z" can be predicted while the distribution of ion intensities (distribution profile of peaks) as shown in FIG. 4 by a broken line is previously determined. It is possible to perform a data analysis with the predictive information using "m/z" of the detected ion only. The analytic accuracy can be increased as the information of the relative ion intensities is added. It is more effective that the information of the relative ion intensity is considered in addition to the value of m/z when the detected ion peak is extremely weak or genome DNA sample is multiplexed.

In FIGS. 5A, 5B, and 5C, there are four different predictive mass spectra for genome DNA samples with 39 base length. In the mass spectrum shown in FIG. 5A, four peaks on the left side correspond to an ion with 13 charges and four peaks on the right side correspond to an ion with 12 charges. A solid line indicates a prediction in which it is not a polymorphism (i.e., major), while a dashed line, a short-dashed line, and a long-dashed line indicate predictions in which they are defined as polymorphism (i.e., minor). In this case, a dashed line, a short-dashed line, and a long-dashed line indicate a predictive mass spectroscopy for a genome DNA, which is a single nucleotide polymorphic genome DNA in which cytosine in the major genome DNA is replaced with ganine, adenine, and thymine. In FIG. 5B, an example of detecting a polymorphic homo-type is shown. In the case of the homo-type, as shown in the figure, a peak that corresponds to each of charges in the ion appears one by one. In this case, the detected mass spectrum is approximate to the predictive one in which a mutation base is thymine. Therefore, the genome DNA of the sample may be defined as a minor type where a polymorphism point is replaced with thymine.

Furthermore, FIG. 5C illustrates an example of detecting a polymorphic hetero-type. In the case of a hetero-type, as shown in the figure, a polymorphic peak can be also detected in addition to a major peak represented by a solid line. In this case, the minor peak where a polymorphism point is replaced with adenine is represented in addition to the major peak, so that it is determined that the genome DNA in the sample may be of a hetero-type where a polymorphism point is replaced with adenine. Consequently, seven different output predictions are generated from the output prediction part 32 based on the sample information transmitted from the sample treatment part 11. These output predictions are typically transferred into a data analysis part 33 in binary form. Then, the predictions are compared with the actual output from the output analysis part 35. An appropriate output prediction is selected so as that the highest matching score (homology) can be attained, followed by adding a label number of the sample and recording in the recording part 34.

Actually, the data analysis part 33 calculates a total of the ion intensities to be detected with respect to a plurality of peaks in the range of a predetermined m/z including an error of the measurement apparatus around the predictive value of m/z with respect to each of the output predictions from the output prediction part 32. Then, the output prediction is selected where the total of the ion intensities is at the highest level. In addition, as described above, the output prediction may be performed using the ion intensity distribution. In this case, furthermore, relative ion intensities detected in the range of given values of each m/z are obtained against a plurality of predicted peaks obtained from the output prediction part 32. Then, an output prediction is selected such that the sum of the square of a difference between a relative value obtained by the actual results and a relative value obtained by the prediction is smallest. In the measurement at a low concentration near a detection limit, the ion intensity distribution is effective with the selection of the output prediction.

The genome DNA analysis system and the method of the present invention have high analytic accuracies, so that a multiplex measurement can be performed on a liquid solution containing a plurality of genome DNA fragments to improve the throughput. FIGS. 6A and 6B illustrate examples of an output prediction, where each of samples contains a mixture of genome DNA fragments of 39 and 40 base lengths. FIGS. 6A illustrates the whole chart of the mass spectrum to be predicted. In the figure, a peak with a circled mark is an ion peak derived from the genome DNA fragment of 39 base length. FIG. 6B is a partially enlarged view of FIG. 6A and, as described above, and represents three to seven possible output predictions with respect to each genome DNA fragment.

The base length of the genome DNA fragment with a major peak may be different from that of the polymorphic (minor) genome DNA fragment. In this case, major or minor can be determined by the measurement. Furthermore, there may be cases where the sample is contaminated with the genome DNA fragment of a PCR amplification probe. However, the output prediction may be performed so as to include ions of a probe to be detected in the focused range of m/z value. Actually, it is preferable to perform a sample preparation so as to keep the m/z of the probe ions away from those derived from the genome DNA fragment subjected to the SNP analysis.

Figure 7:
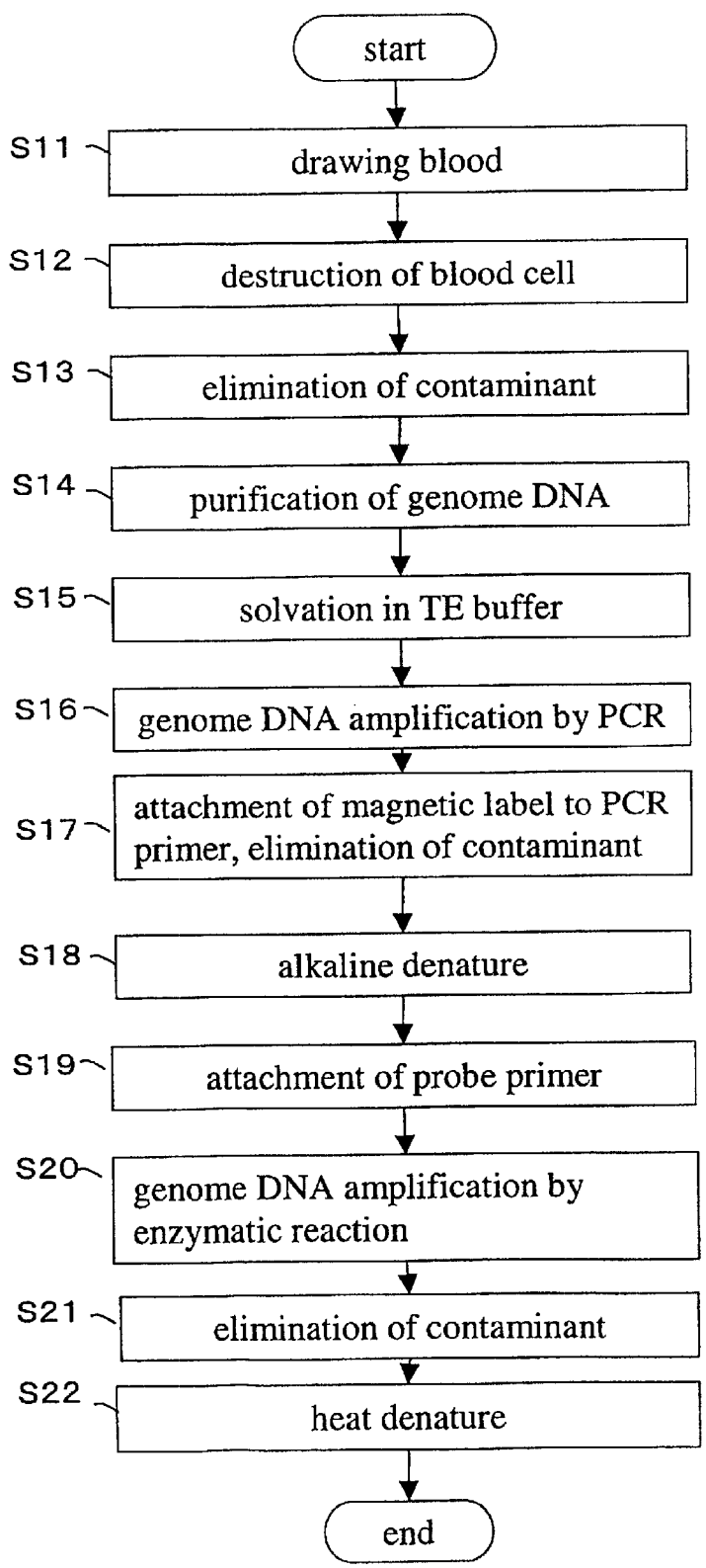
FIG. 7 is a flow chart that illustrates the process of preparing the sample to be used in the present invention.

FIG. 7 shows a flow chart of the typical sample preparation process for the genome DNA sample. Approximately 200 μl of blood is drawn (S11). A protease, a chaotropic salt, a surfactant and the like are added to the drawing blood to destruct mainly white cells (S12). Protein components in the blood are removed by a phenol extraction (S13), and genome DNA is then extracted using isopropanol and ethanol. The resulting genome DNA solution is subjected to a centrifugal separator, and is then air-dried to obtain as a genome DNA preparation (S14). Subsequently, the genome DNA is dissolved in a TE buffer (S15). The resulting solution is subjected to a PCR amplification. Next, a PCR primer is combined with a magnetic label for utilizing the magnetic force to eliminate any contamination from the genome DNA by cleaning (S17). The purified genome DNA is a double strand DNA. In this case, however, it is subjected to an alkaline denature, so that the double strand DNA becomes a single one (S18). The single DNA is combined with the primer of the probe (S19). After then, the DNA enzymatic reaction allows the elongation of the primer of the probe (S20). Also, cleaning is performed to eliminate the contaminant (S21). At last, the single strand genome DNA is prepared using the denaturation by heat (S22). Most of these steps can be automatically performed in the sample treatment part 11. The measurement target portion may be changed by changing the primer and the primer of the probe.

Figure 8:
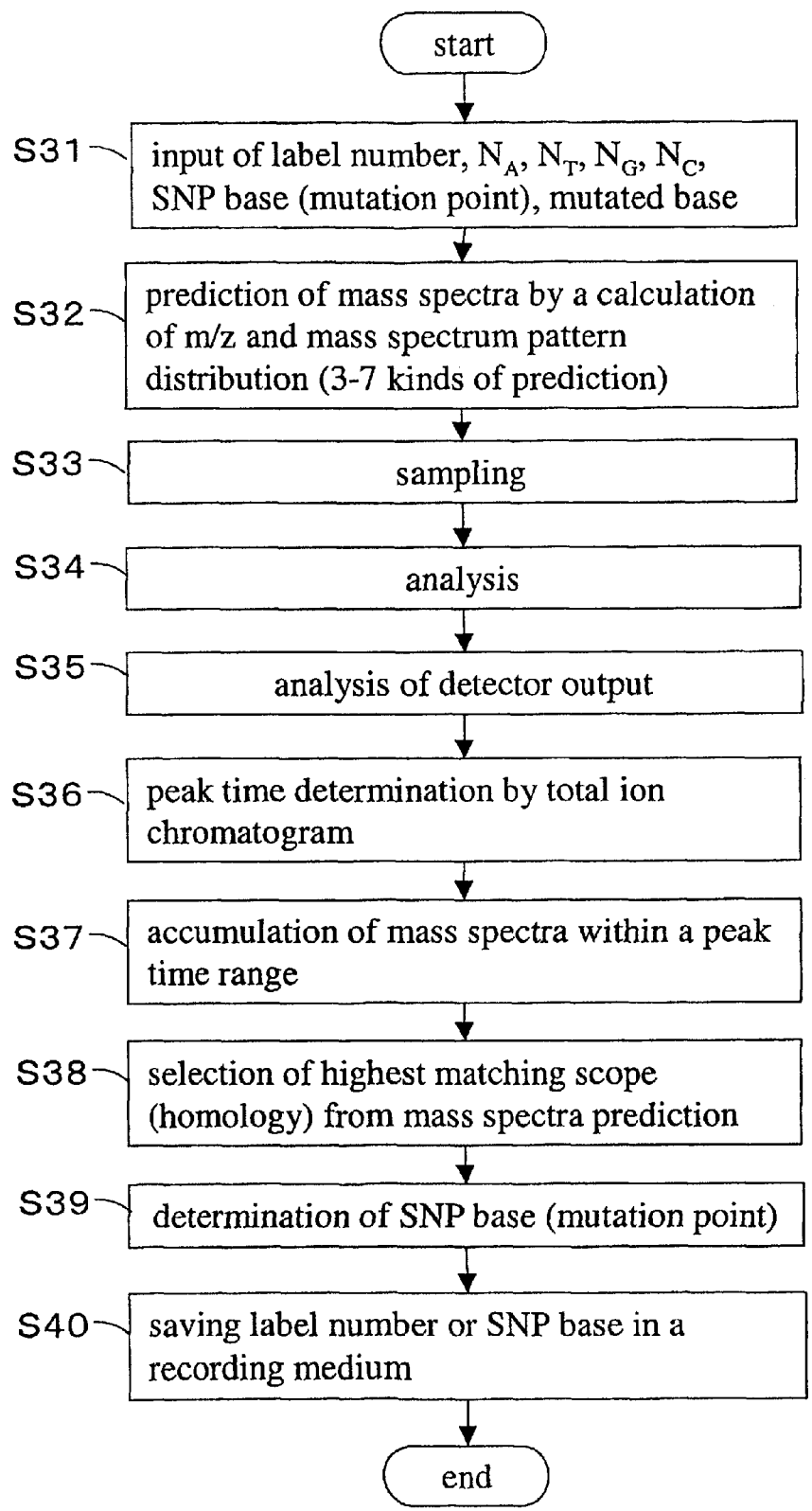
FIG. 8 is a flow chart that illustrates an example of the procedures in the genome DNA analysis system of the present invention.

FIG. 8 shows a flow chart of a basic treatment in the sample data analysis in accordance with the present invention.

For a sample that contains genome DNA, at first, the history information (e.g., a label number) of the sample, bases corresponding to $N_A$, $N_T$, $N_G$, $N_C$, and SNP, and the number of the mutation bases are entered in the output prediction part 32. In the output prediction part 32, 3 to 7 mass spectrum patterns are predicted based on the number of the bases entered (S32). It is preferable that the distribution of ion intensities is included in the predicted mass spectrum pattern in addition to the m/z of the detected ion. In addition, it is also preferable to consider an error in the actual data, because the mass number (m/z) corresponding to the horizontal axis of the actually measured mass spectrum may be slightly varied.

If the start signal is inputted, then the sample stored in a container is introduced from the sampling part 15 to the tube 16 every 10 μl per a predetermined time period T (S33). The sample introduced in the tube 16 is further introduced into the ionization part 21 where the sample is ionized, followed by the measurement in the mass analysis part 24 (S34). An output from the detector 28 installed on the mass analysis part 24 is subjected to an output-analysis in the output-analysis part 35 (S35). From the data obtained by analyzing the output, the whole ion chromatogram is obtained. Then, a time period in which ions derived from the same sample are detected is determined on the basis of the ion chromatogram (S36). The data obtained by the analysis of the output (mass spectrum) is subjected to an accumulation step within the determined time period (S37). The data being accumulated is compared with several predicted mass spectrum patterns previously obtained and a predicted pattern with the highest matching score is selected (S38). Consequently, the SNP base is determined (S39), and the nucleic acid base of the SNP portion corresponding to the selected prediction is recorded together with sample's history information such as a label number on a recording medium in the recording part 34 (S40). The recording medium may be selected from a digital versatile disk (DVD), a magneto-optical (MO) disk, a hard disk, a floppy disk, and the like. Furthermore, the analyzing results may be printed out on a sheet of paper or a client or the like may be informed through a network.

At the time of the actual sample analysis, many samples may be measured with respect to the same SNP portion. In this case, there is no need to perform the prediction of mass spectrum pattern per a sample. If the prediction data is determined once, it can be used for each sample to be measured. In this case, as indicated in the flow chart shown in FIG. 8, the procedures of the steps 21 and 22 are only performed once.

The analysis system described above independently operates the output prediction part 32, the data analysis part 33, the control part 31, the output analysis part 35, and the recording part 34. Alternatively, an integrated circuit, a personal computer, or the like may be used to unify these parts together to provide a single control system for the control of the analysis system, the analysis process, and the like.

[Second Embodiment]

Next, a method for simultaneously analyzing SNPs of the predetermined number (n) of genome DNA samples with their respective different base lengths will be described.

An analysis system used for the present embodiment may be the system shown in FIG. 1. In this case, however, the sample-treatment part 11 can simultaneously perform the procedures of PCR amplification, extension and the like on the predetermined number (n) of different genome DNA fragments to prepare a sample that contains a mixture of the predetermined number (n) of the different genome DNA fragments with different base lengths. In the sampling part 15, a predetermined volume of the sample which makes up the genome DNA fragments having different base lengths is introduced into the capillary tube 16 at predetermined intervals of T. The mass spectrometric part 24 simultaneously performs the measurement on the predetermined number (n) of the different genome DNA fragments to obtain their mass spectra. Furthermore, the output prediction part 32, the output analysis part 35, and the data analysis part 33 of the control system simultaneously perform the analysis on SNPs of the predetermined number (n) of the different genome DNA fragments.

Figure 9:
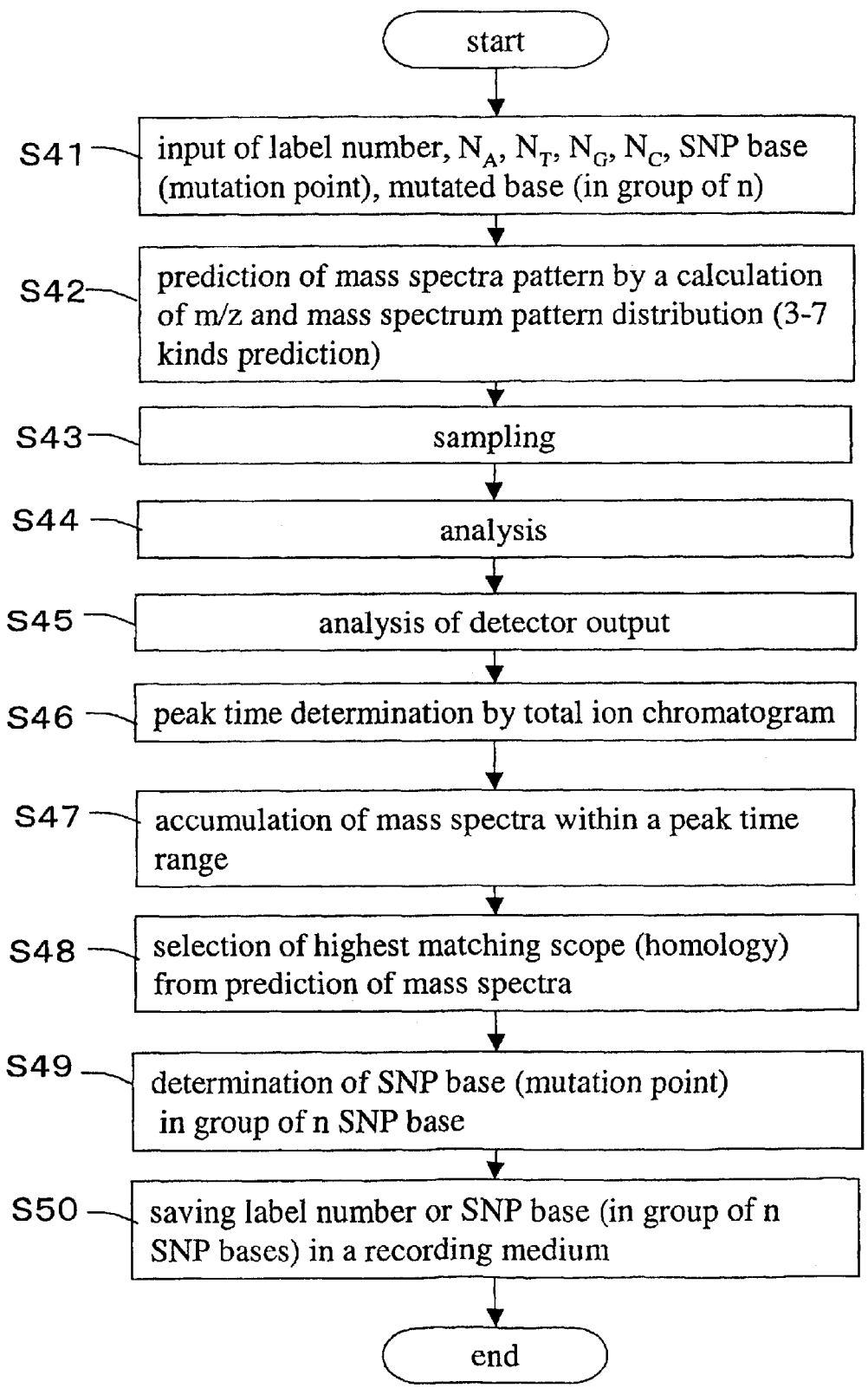
FIG. 9 is a flow chart that illustrates an example of the procedures in the genome DNA analysis system for the multiplexed samples.

FIG. 9 illustrates a flow chart for the analysis on a sample having the predetermined number (n) of the genome DNA with different base lengths. The flow chart shown in FIG. 9 is almost similar to that of FIG. 8, except that the process for one type of genome DNA fragments in FIG. 8 is modified so as to be applied to plural types (n) of genome DNA fragments.

Information about the label number of each sample, four different types of bases corresponding to the numbers $N_A$, $N_T$, $N_G$, $N_C$, and SNP, which constitute n-different types of genome DNA fragment in the sample, and mutation bases thereof are entered into the output prediction part 32 of the control system (S41). Three to seven possible patterns of mass spectra are predicted for each of n types of the genome DNA fragments at the output prediction part 32 (S42). The process from the sampling in the step 43 to the accumulation of mass spectrum within the peak time range in the step 47 corresponds to the steps 32 to 37 of the process shown in FIG. 8. The accumulated data is compared with the previously obtained predicted n patterns of the mass spectra. The prediction having the highest matching score is selected (S48). Consequently, n SNP bases are determined (S49), and n pieces of information of SNP bases are stored in the recording medium at the recording part 34 in addition to the sample's history information such as a label number (S50).

Accordingly, the throughput can be increased for n times when the sample is multiplexed for n times and includes n types of different genome DNA fragments. However, the retrieval of matching scores becomes difficult compared with that of not-multiplexed sample, so that insufficient results may be obtained. In this case, the decrease in analytic accuracy can be restricted by using an ion intensity profile as predicted information. For example, a retrieve of matching scores depending on the base length "N" is performed on the distribution of intensities of the multiply-charged ions and subsequently SNP for each base length "N" is determined to obtain only one result. Therefore, the analysis of multiplexed sample is not limited to m/z of the mass spectrum pattern. It may be possible to include the information of multiply-charged ion intensity distribution.

[Third Embodiment]

Figure 10:
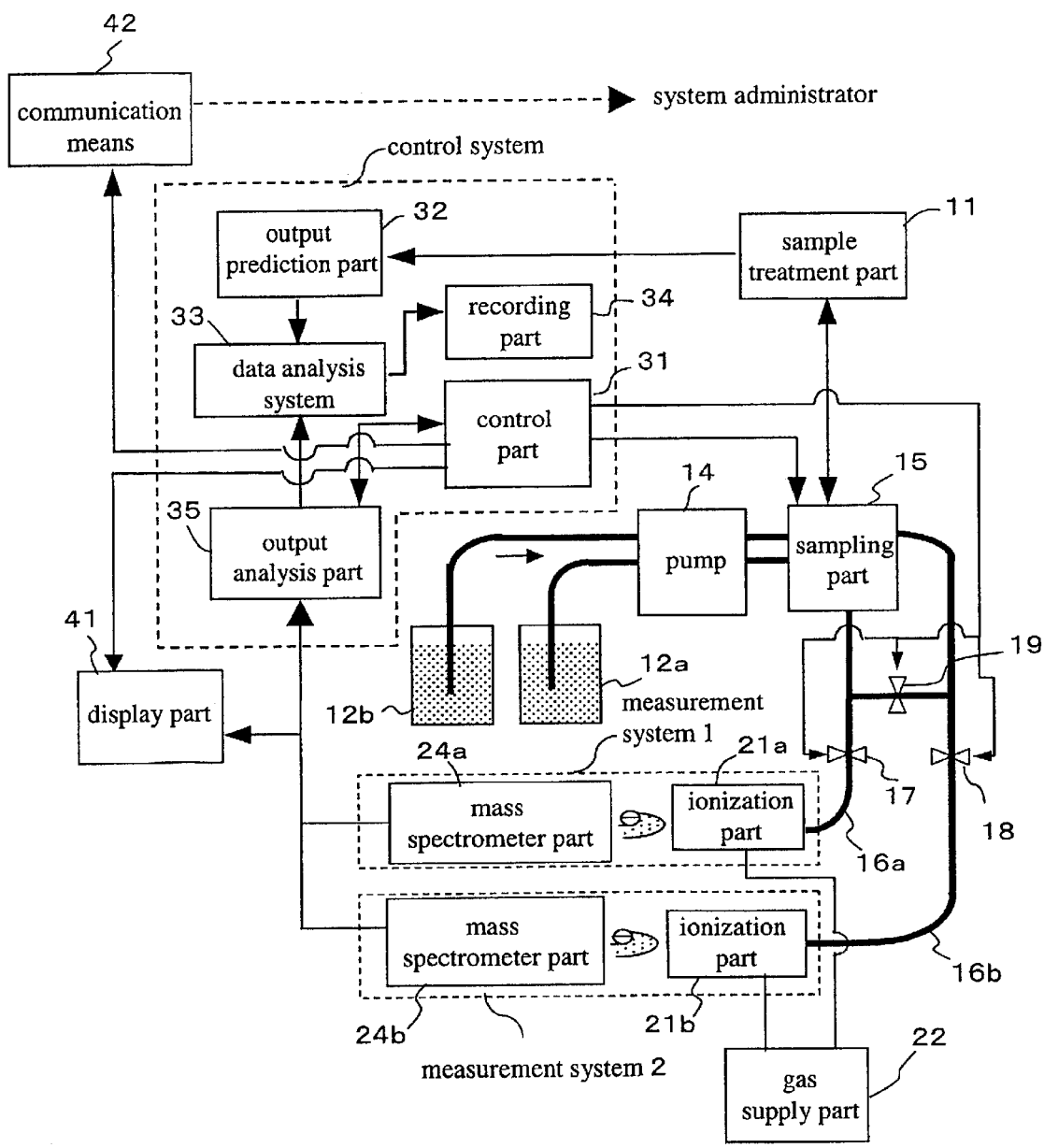
FIG. 10 is a schematic diagram that illustrates the configuration of the DNA analysis system having a backup function.

FIG. 10 illustrates a genome DNA analysis system as a third embodiment of the present invention. The genome DNA analysis system has a backup function to cope with if any emergency occurs. In FIG. 10, the same reference numerals denote the same functional parts as those of FIG. 1, so that the details of such parts will be omitted in the following description.

During the mass spectrometry of the sample, there are the cases where the measured ion intensities are abnormally low. Such abnormalities (emergency) may depend on the following items. That is, 1) the problem with respect to the sample preparation; 2) unexpected problem in the measurement process; 3) the contamination in the measurement apparatus; and the like. When an unexpected problem in the measurement process occurs, it does not get behind by the sample measurement of the rest. A problem can be solved by the re-measurement. However, if the above abnormalities occur by the problems of the sample preparation and the contamination in the measurement apparatus, even the sample measurement of the rest will cause any abnormality. In that case, the sample preparation should be performed again, or the check and adjustment of the measurement system are necessary.

To make such a judgment, the standard sample may be prepared in advance. If the measured ion intensity is smaller than the predetermined level, then the measurement is performed on the standard sample. The standard sample may be provided in the sample-retaining container. Alternatively, it may be supplied from the sample treatment part in response to a request from the sampling part.

There is no emergency in the measurement apparatus if the measurement of the standard sample is completed normally. On the other hand, there is any emergency in the measurement apparatus if the measurement of the standard sample is not completed normally. When it is judged that there is no emergency in the measurement apparatus, the same sample as that on which the emergency has occurred is used and subjected to the re-measurement. When the emergency occurs by the re-measurement, it is judged that the trouble arises in the sample adjustment part. The operation of the system is made to stop at the regulatory part.

The genome DNA analysis system shown in FIG. 10 includes a plurality of measurement system (in figures, 2-line system) having ionization part 21a and 21b, and mass spectrometric parts 24a and 24b; valves 17, 18 and 19 to switch tubes 16a and 16b through which the sample flows; display means 41 on which the analyzing results are displayed; transmitting means 42 for transmitting the information that notifies the occurrence of an emergency to the system administrator; and the like. Usually, two measuring systems 1 and 2 are operated at the same time to perform the measurements of a plurality of samples in parallel. The tube 16a connected to the measurement system 1 receives a cleaning fluid from a container 12a, while the tube 16b connected to the measurement system 2 receives the cleaning fluid from a container 12b.

Figure 11:
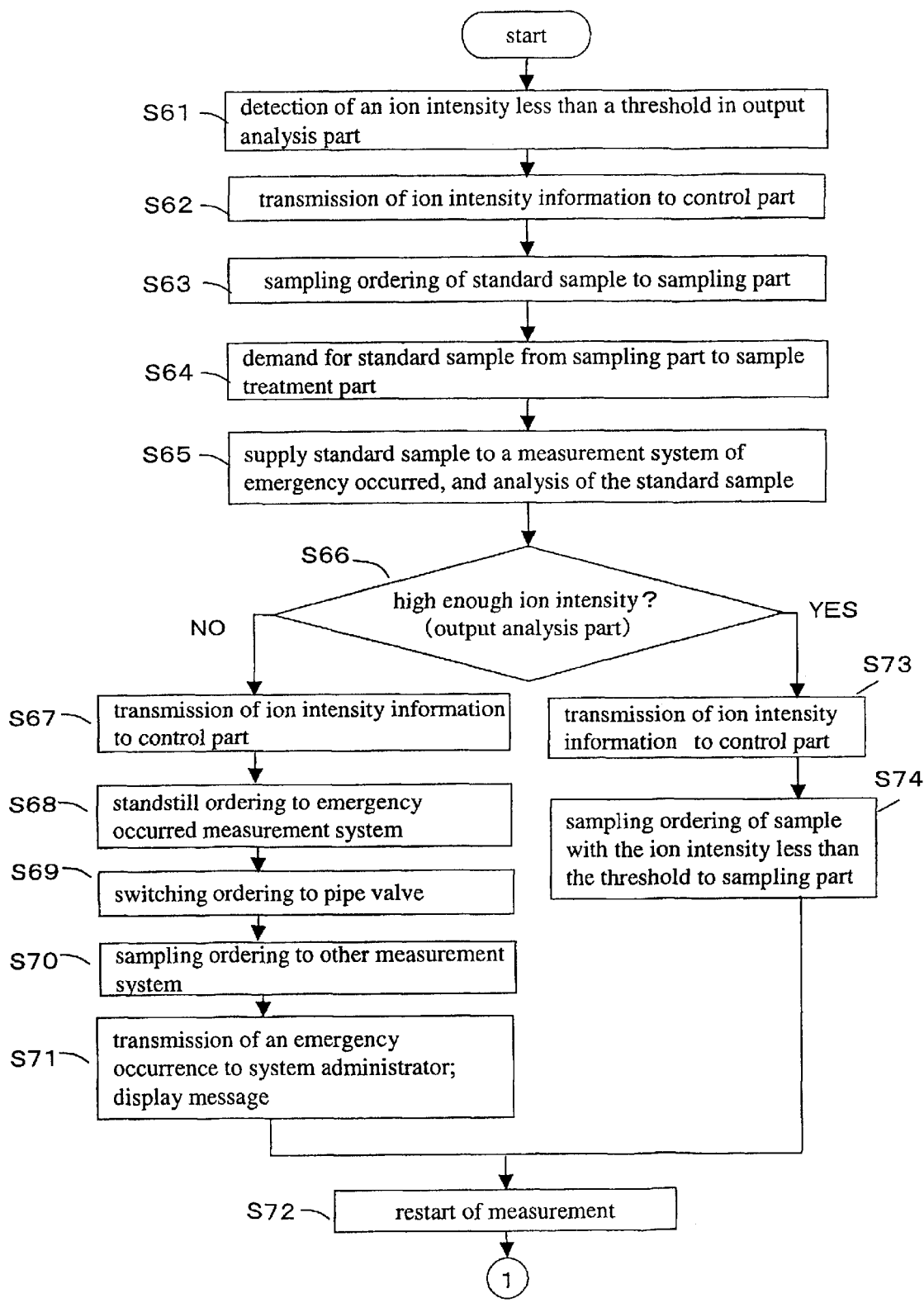
FIG. 11 is a flow chart that illustrates the procedure against an emergency occurred in the system.
Figure 12:
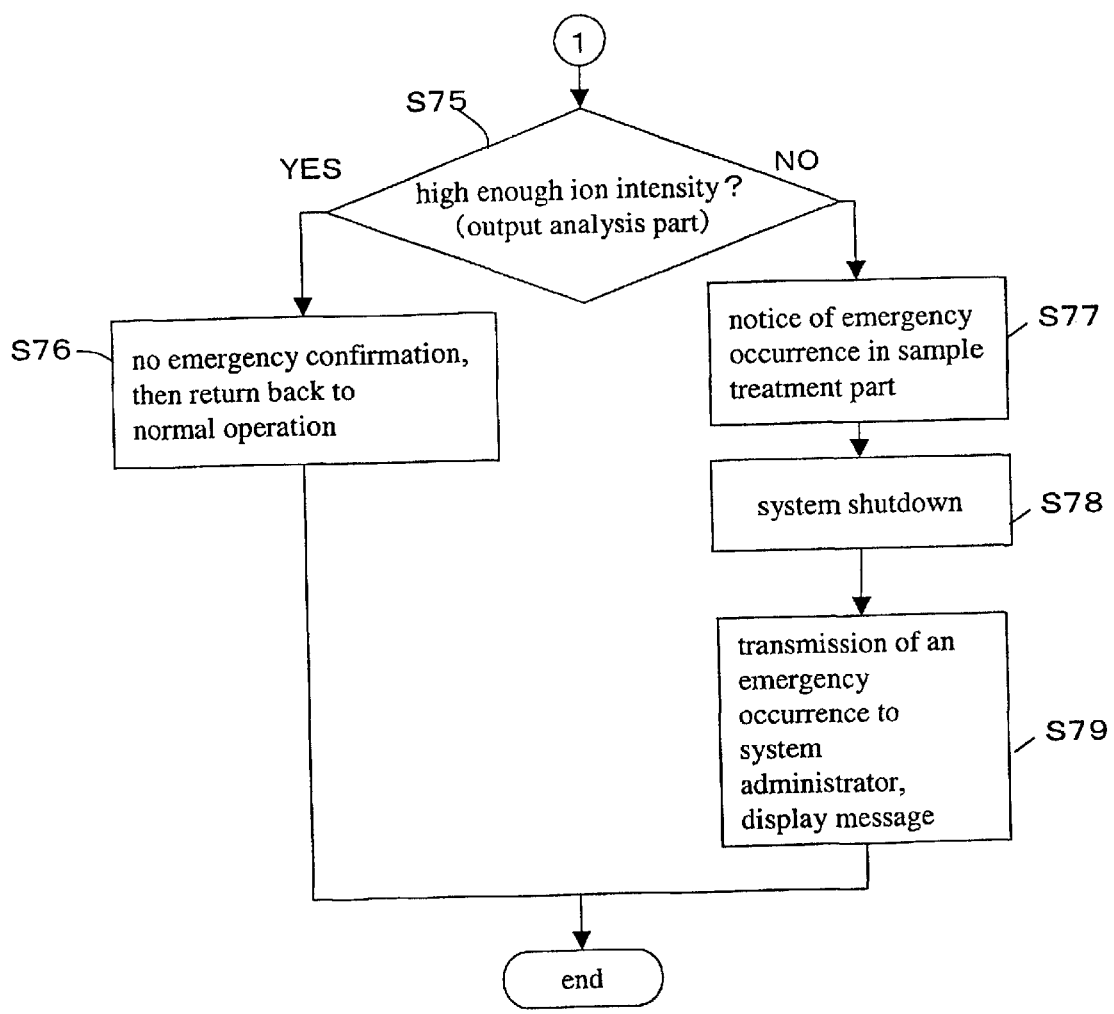
FIG. 12 is a flow chart that illustrates the procedure against an emergency occurred in the system.

FIGS. 11 and 12 illustrate flow charts for the process that copes with the occurrence of an emergency. If the measured mass spectrum is smaller than the predetermined threshold, then the output analysis part 35 determines that any emergency has occurred (S61). Then, the output analysis part 35 transmits an emergency occurrence signal to the control part 31, and also transmits the information of ion intensity and the label number of the sample (S62). Upon receiving the signal, the control part 31 sends a sampling ordering to the sampling part 15 to instruct that the standard sample should be sampled. The sampling part 15 requests the sample treatment part 11 for the supply of the standard sample (S64). The standard sample supplied from the sample treatment part 11 is introduced into the ionization part of the measurement system where the emergency has occurred through the sampling part 15, followed by measurement (S65). The output analysis part 35 compares the ion intensity with the predetermined threshold (S66).

If it is found that an emergency has occurred in the system while the ion intensity is smaller than the threshold as a result of measuring the standard sample, then the output analysis part 35 informs the control part 31 of the emergency. Then, the control part 31 instructs the sampling part 15 to stop the sampling operation to the emergency occurred measurement system (S68). At the same time, the control part 31 sends to the valves a switching ordering of pipe valves so that the sample flows into the normal measurement system (S69) and then instructs the sampling part 15 to sample on the normal measurement system (S70). The control part 31 further activates the communication means 42 to generate information that informs the system administrator about the fact that the emergency has occurred and displays the fact that the emergency has occurred on a screen of the display means 41 (S71). The communication means 42 may be a cellular phone, a transceiver, a portable information terminal, and the like. The display means 41 may be typically a monitor, an oscilloscope for displaying a waveform, and the like. After that, the re-measurement is initiated in the normal measurement system (S72).

In the judgment of the step 66, when ion intensity exceeds the threshold by the measurement of the standard sample and it is proved that there is no emergency in the apparatus, the output treatment part 35 informs a control part 31 about it (S73). The control part 31 sends the sampling part 15 a sampling ordering of a sample in which the ion intensity has been measured low (S74) to perform the sampling of the sample that ion intensity has been measured weaker (S72). For promptly performing the re-measurement, it is desirable for the sampling part 15 to keep the sample volume at twice or more than usual.

As the result of the re-measurement, the judgment is made by the output analysis part 35 whether the ion intensity is sufficient (S75). If the ion intensity is still small when the emergency occurs, then the control part 31 judges that the emergency occurs in the sample treatment part 11 (S77). Then, the control part 31 stops the operation of the entire system (S78). Simultaneously, the information about the occurrence of an emergency is transmitted to the system administrator through the transmission means 42 and displayed on a screen of the display means 41 (S79).

FIG. 13 shows examples of the displays of normal and emergency conditions. On the screen, the label number of the sample on which the measurement has been completed, the latest mass spectrum, and the like are displayed. Under the normal state, the screen is renewed one after another. Under the emergency state, the measurement results of the standard sample (mass spectrum or the like) are kept on the screen in addition to the information about the emergency conditions. The system administrator observes the displayed information and the measurement results on the screen to grasp the conditions promptly to quickly respond to the emergency occurred.

In the present embodiment, if the emergency occurs in the sample treatment part 11, the whole system stops its functions. In this case, however, the measurement can be performed by providing more than one sample treatment parts with the system and switching to normal part thereof at the time when the emergency has occurred so as to continue the analysis without suspending the whole system.

[Fourth Embodiment]

Figure 14:
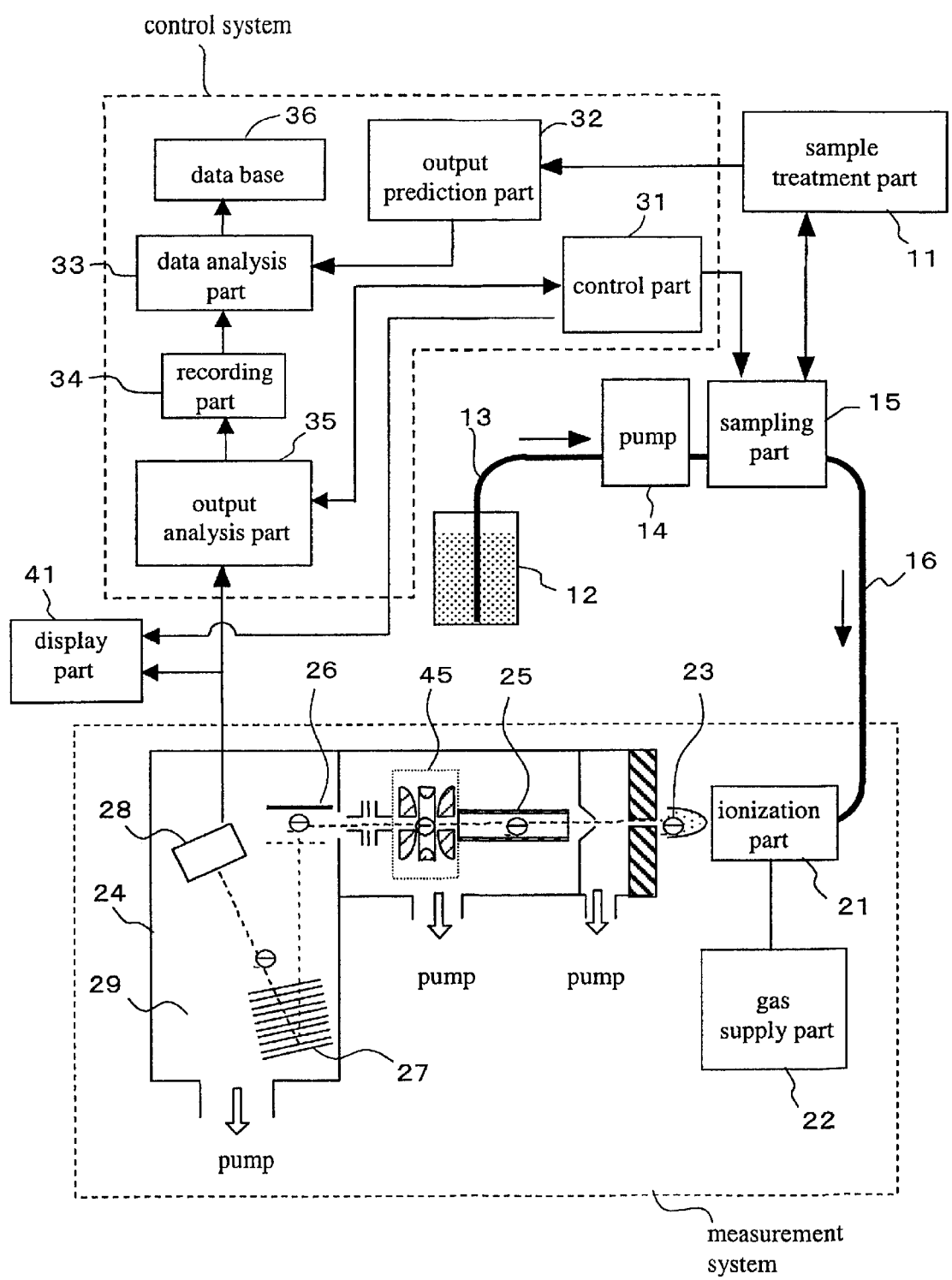
FIG. 14 is a schematic diagram that illustrates another example of the genome DNA analysis system of the present invention.

FIG. 14 is a schematic diagram that illustrates a genome DNA analysis system as a fourth embodiment of the present invention. In FIG. 14, the same functional parts are represented by the same reference numerals as those of FIG. 1, so that the details thereof are omitted in the following description. The genomic DNA analysis system sends an output of the output analysis part 35 to the recording part 34 to record in the recording medium for a while. After the measurement has been completed, the analysis is performed on the data temporally recorded on the recording part 34, which is different from the system configuration shown in FIG. 1. The data of the SNP base of each sample determined by the analysis is stored in a database 36.

Furthermore, the mass spectrometric part 24 of the measurement system includes a quadrupole ion trapping 45. A beam-shaped ion which has passed through the ion guide 25 is introduced into the quadrupole ion trapping 45, and trapped for a while. Thus, the ion receives the cooling due to the molecular collision, so that the energy distribution and the spatial distribution are decreased. Furthermore, the ion is transported from the quadrupole ion trapping 45 in a short time by a high vacuum region 29 by applying a pulse voltage to the quadrupole ion trapping 45. In the high vacuum region 29, the high voltage pulse is applied to the electrode 26, so that the ion is accelerated downward and subjected to a mass spectrometry using a time-to-flight mass spectrometer. In this case, however, when the ion spreads out spatially when a pulse is accelerated, it becomes difficult to obtain a sufficient mass resolution. In this embodiment, the ion cooling is performed by using the quadrupole ion trapping 45. Thus, it realizes the sufficient mass resolution with a compact apparatus construction.

Figure 15:
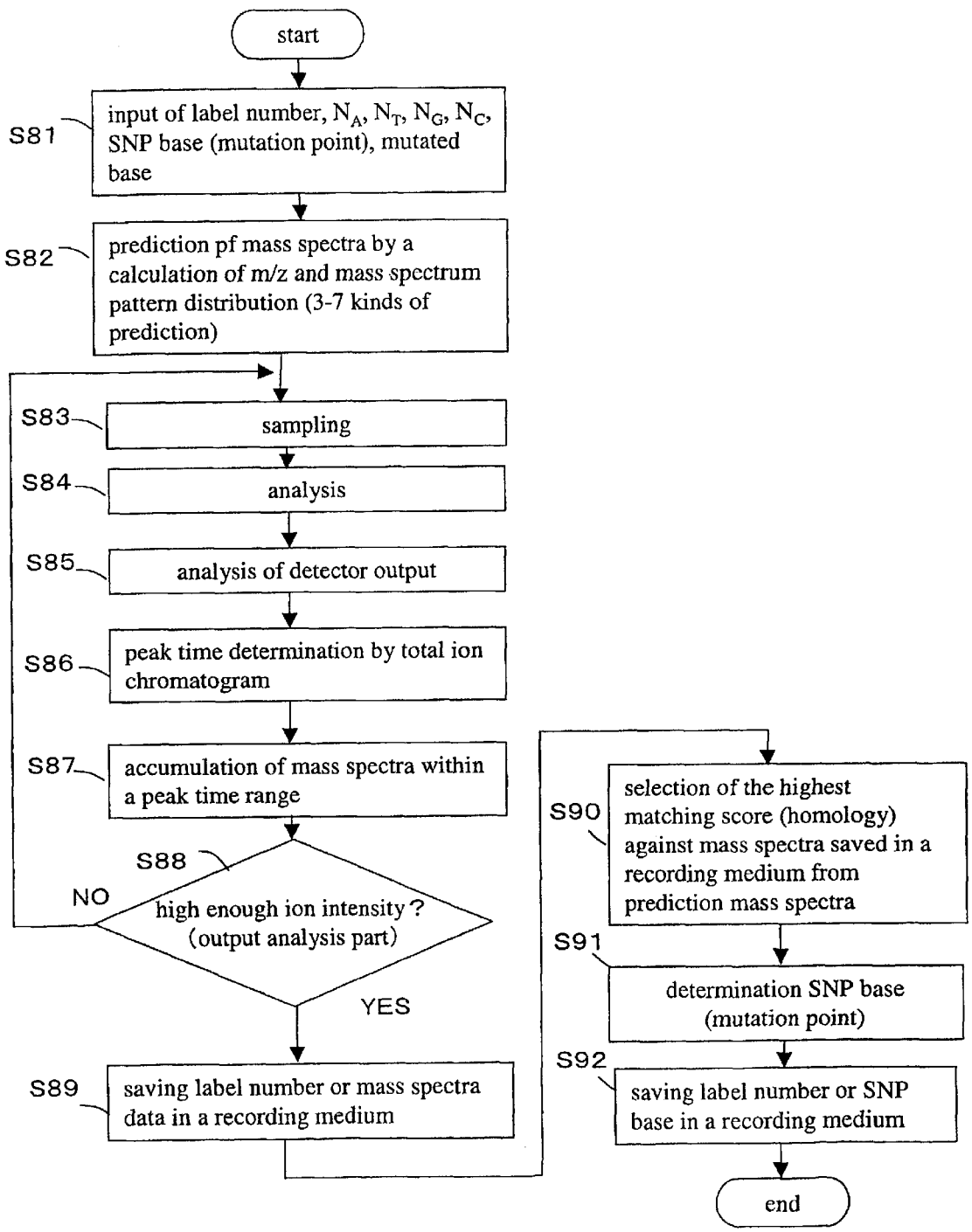
FIG. 15 is a flow chart that illustrates another example of the procedures in the genome DNA analysis system of the present invention.

FIG. 15 shows a flow chart of the process of analyzing a genome DNA sample. In the process of analyzing the genome DNA sample according to the embodiment, the measuring results of the genome DNA sample is sequentially stored in the recording medium, so that all the data can be subjected to the data analysis after completing the measurement of the whole sample. The procedure from the step 81 (i.e., entering of the basic data including the label number of the sample, the SNP base, and the like) to the step 87 (i.e., accumulation of mass spectrum) is the same as that shown in FIG. 8. After completing the measurement, the data analysis is executed. Thus, after the accumulation step (S87) whether the measured data has sufficient ion intensities or not is judged (S88). If sufficient ion intensities can be obtained, then the label number and the mass spectrum data are stored in the recording medium (S89). If it is not sufficient, then the same sample is subjected to the measurement again. Specifically, if the output of the detector 28 is smaller than a predetermined value, then the output analysis part 35 sends the control part 31 an emergency signal. In addition, a sampling change ordering is sent to the sampling portion 15.

After completing the measurement, the mass spectrum data recorded in the recording medium by the recording part 34 is introduced into the data analysis part 33. In the data analysis part 33, data from the recording medium is compared with mass spectrum pattern predictions. Then, the prediction with the highest matching score is selected (S90). Therefore, the SNP base corresponding to the selected prediction is determined (S91) and recorded together with the label number in the recording medium as a database (S92). For the improvement of the throughput in the present embodiment, n samples may be simultaneously subjected to measurement.

Accordingly, the present invention can be characterized as follows.

(1) A DNA analysis method for analyzing DNA polymorphism, including:

a first step for predicting mass spectrum patterns when plural kinds of multiply-charged ions generated from a test DNA fragment, where each of them has five or more charges, in each of two cases where one is that the test DNA fragment is polymorphic and the other is that the test DNA fragment is not polymorphic, based on information of the number of four bases that constitutes the test DNA fragment and information of a polymorphism point;

a second step for generating plural kinds of multiply-charged ions in gaseous form from a sample containing the test DNA fragment;

a third step for performing a mass spectrometry on the multiply-charged ion in gaseous form to measure a mass spectrum; and a fourth step for selecting a predicted mass spectrum pattern that is most closely analogous to the measured mass spectrum pattern by comparing the predicted plural mass spectrum patterns in the first step with the measured mass spectrum patterns in the third step.

(2) The DNA analysis method as described in the item (1), wherein a predicted mass spectrum pattern that is most closely analogous to the measured mass spectrum pattern is selected from the plurality of predicted mass spectrum patterns by comparing a mass-to-charge ratio (m/z; m is an ion mass, z is the number of electric charges) of a peak of the measured mass spectrum with a mass-to-charge ratio (m/z) of a peak of each of the plurality of predicted measured mass spectrum patterns.

(3) The DNA analysis method as described in the item (1), wherein a predicted mass spectrum pattern that is most closely analogous to the measured mass spectrum pattern is selected from the plurality of predicted mass spectrum patterns by comparing a ratio of m/z and the distribution of ion intensities of a peak of the measured mass spectrum with m/z and the distribution of ion intensities of a peak of each of the plurality of predicted measured mass spectrum patterns.

(4) The DNA analysis method as described in the item (1), wherein a nucleic acid base of a single nucleotide polymorphism point in the test DNA fragment is determined.

(5) The DNA analysis method as described in the item (1), wherein identification information of the sample including the test DNA fragment is recorded so as to be associated with the measured mass spectrum, a mass spectrum pattern for the sample is predicted with reference to the identification information, and the predicted mass spectrum pattern is compared with the recorded mass spectrum.

(6) The DNA analysis method as described in the item (1), wherein at least from the second step to the fourth step are subsequently repeated, a mass spectrum measured at an ordinal number "i" is subjected to the following treatment to obtain S(i), and then the S(i) is compared with each of the plurality of predicted mass spectrum patterns, $$S(i) = I(i) - \sum_{n=1}^{m} w(n) I(i-n)$$

wherein m represents a predetermined natural number; w(n) represents a factor that represents the level of influence of the sample measured at n-th before the measurement of the sample which is measured at i-th.

(7) The DNA analysis method as described in the item (1), wherein a mass spectrum of a standard sample is measured when a maximum ion intensity of the measured mass spectrum is smaller than a predetermined threshold.

(8) The DNA analysis method as described in the item (1), wherein a mass spectrum analysis of the next sample is suspended when a maximum ion intensity of the measured mass spectrum of the standard sample is smaller than a predetermined threshold.

(9) The DNA analysis method as described in the item (1), wherein a DNA sample is ionized using an ionization process using an air atomization.

In summary, as described above, a genome DNA analysis system and method of the present invention allows that several types of multiply-charged ions with five or more charges are generated, detected, and checked with the predicted results. Thus, it can achieve a stable measurement even though the concentration of the sample is substantially smaller than the appropriate concentration thereof. In addition, a genome DNA analysis system allows a high-throughput measurement over a long period.

While there has been described what are at present considered to be preferred embodiments of the invention, it will be understood that various modifications may be made thereto, and it is intended that the appended claims cover all such modification as fall within the true spirit and scope of the invention.

What is claimed is:

1. A DNA analysis method for analyzing DNA polymorphism, comprising the steps of:

generating plural kinds of multiply-charged ions of a test DNA fragment by ionization, where each of the multiply-charged ions has five or more charges;

performing a mass spectrometry an the multiply-charged ions formed by the ionization so as to measure a mass spectrum of the test DNA fragment;

predicting possible mass spectrum patterns in each of two cases, where one of the two cases is that the test DNA fragment is polymorphic and an other of the two cases is that the test DNA fragment is not polymorphic, based on both an information about the number of each of four different nucleic acid bases that constitute the test DNA fragment and an information about a polymorphism point; and comparing a plurality of the predicted mass spectrum patterns with the measured mass spectrum to determine a nucleic acid base on the polymorphism point.

2. The DNA analysis method according to claim 1, wherein the step of predicting includes predicting a mass-to-charge ratio (m/z; m is an ion mass, z is a number of electric charges) of each of the plural kinds of multiply-charged ions in each of the two cases, and the step of comparing includes comparing the predicted mass-to-charge ratio (m/z) of the predicted mass spectrum patterns with a mass-to-charge ratio (m/z) of the measured mass spectrum.

3. The DNA analysis method according to claim 1, wherein the step of predicting includes predicting a mass-to-charge ratio (m/z; m is an ion mass, z is the number of electric charges) of each of the plural kinds of multiply-charged ions and a relative ion intensity corresponding to the mass-to-charge ratio (m/z) in each of the two cases, and the step of comparing includes comparing the predicted mass-to-charge ratio (m/z) of the predicted mass spectrum patterns with a mass-to-charge ratio (m/z) of the measured mass spectrum and compares the predicted relative ion intensities of the predicted mass spectrum patterns with relative ion intensities of the measured mass spectrum.

4. The DNA analysis method according to claim 1, further comprising the steps of:

sampling by supplying a sample including the test DNA fragment for the ionization intermittently at a predetermined time period; and performing the following treatment to obtain S(i) for the measured mass spectrum (I(i)) at an ordinal number "i", $$S(i) = I(i) - \sum_{n=1}^{m} w(n) I(i-n)$$

wherein m represents a predetermined natural number and w(n) represents a factor for the measured mass spectrum of the sample measured at n-th before the measurement of the sample which is measured at i-th; and wherein the S(i) is compared with each of the predicted mass spectrum patterns.

5. The DNA analysis method according to claim 1, wherein the step of generating multiply-charged ions of the test DNA fragment by the ionization uses an air atomization.

6. The DNA analysis method according to claim 1, wherein a nucleic acid base of a single nucleotide polymorphism point in the test DNA fragment is specified.

7. The DNA analysis method according to claim 4, further comprising the step of:

displaying the occurrence of an emergency when a maximum ion intensity detected by the mass spectrometry is smaller than a predetermined threshold.

8. The DNA analysis method according to claim 7, further comprising the steps of:

generating information about the occurrence of the emergency.

9. The DNA analysis method according to claim 4, wherein the step of sampling introduces a standard sample for the ionization when a maximum ion intensity of the measured mass spectrum by the mass spectrometry is smaller than a predetermined threshold.

10. The DNA analysis method according to claim 9, wherein when a maximum ion intensity of a mass spectrum of the standard sample detected by the mass spectrometry is equal to or higher than the predetermined threshold, the sample where the maximum ion intensity of the mass spectrum is detected as one smaller than the predetermined threshold is re-supplied to the ionization by the sampling.

11. The DNA analysis method according to claim 9, further comprising the steps of:

utilizing a plurality of measurement systems, where each of the measurement systems comprises the steps of sampling, ionization, and mass spectrometry, wherein when a maximum ion intensity of a mass spectrum of the standard sample detected by mass spectrometry in one measurement system of the plurality of measurement systems is smaller than the predetermined threshold, the sample where a maximum ion intensity of a mass spectrum is detected as one smaller than the predetermined threshold at the one measurement system is transmitted for sampling of another measurement system except the one measurement system.

12. The DNA analysis method according to claim 9, further comprising the steps of:

utilizing a plurality of measurement systems, where each of the measurement systems comprises the steps of sampling, ionization, and mass spectrometry, wherein when a maximum ion intensity of a mass spectrum of the standard sample detected by mass spectrometry in one measurement system of the plurality of measurement systems is smaller than the predetermined threshold, a sample intended to be measured by the one measurement system is sent for sampling of another measurement system except the one measurement system.

13. A DNA analysis method for analyzing DNA polymorphism, comprising the steps of:

sampling by supplying a sample including a test DNA fragment for ionization intermittently at a predetermined time period;

generating plural kinds of multiply-charged ions of the test DNA fragment by ionization, where each of the multiply-charged ions has five or more charges;

for performing a mass spectrometry on the multiply-charged ions formed by the ionization so as to measure a mass spectrum of the test DNA fragment;

performing the following treatment to obtain S(i) for the measured mass spectrum (I(i)) at an ordinal number "i", $$S(i) = I(i) - \sum_{n=1}^{m} w(n) I(i-n)$$

wherein m represents a predetermined natural number and w(n) represents a factor for the measured mass spectrum of the sample measured at n-th before the measurement of the sample which is measured at i-th;

predicting possible mass spectrum patterns in each of two cases, where one of the two cases is that the test DNA fragment is polymorphic and an other of the two cases is that the test DNA fragment is not polymorphic, based on both an information about the number of each of four different nucleic acid bases that constitute the test DNA fragment and an information about a polymorphism point, wherein the step of predicting includes predicting a mass-to-charge ratio (m/z; m is an ion mass, z is a number of electric charges) of each of the plural kinds of multiply-charged ions and a relative ion intensity corresponding to the mass-to-charge ratio (m/z) in each of the two cases; and comparing a plurality of the predicted mass spectrum patterns with the measured mass spectrum to determine a nucleic acid base on the polymorphism point, wherein the step of comparing includes comparing the predicted mass-to-charge ratio (m/z) of the predicted mass spectrum patterns with a mass-to-charge ratio (m/z) of the measured mass spectrum and compares the predicted relative ion intensities of the predicted mass spectrum patterns with relative ion intensities of the measured mass spectrum, and wherein the S(i) is compared with each of the predicted mass spectrum patterns.

14. A DNA analysis method for analyzing DNA polymorphism, comprising the steps of:

sampling by supplying a sample including a test DNA fragment for ionization intermittently at a predetermined time period;

generating plural kinds of multiply-charged ions of the test DNA fragment ionization, where each of the multiply-charged ions has five or more charges;

performing a mass spectrometry on the multiply-charged ions formed by the ionization so as to measure a mass spectrum of the test DNA fragment;

performing the following treatment to obtain S(i) for the measured mass spectrum (I(i)) at an ordinal number "i", $$S(i) = I(i) - \sum_{n=1}^{m} w(n) I(i-n)$$

wherein m represents a predetermined natural number and w(n) represents a factor for the measured mass spectrum of the sample measured at n-th before the measurement of the sample which is measured at I-th;

predicting possible mass spectrum patterns in each of two cases, where one of the two cases is that the test DNA fragment is polymorphic and an other of the two cases is that the test DNA fragment is not polymorphic, based on both an information about the number of each of four different nucleic acid bases that constitute the test DNA fragment and an information about a polymorphism point, wherein step of predicting includes predicting a mass-to-charge ratio (m/z; m is an ion mass, z is a number of electric charges) of each of the plural kinds of multiply-charged ions and a relative ion intensity corresponding to the mass-to-charge ratio (m/z) in each of the two cases; and comparing including calculating a total ion intensity of each of the predicted mass spectrum patterns with respect to a plurality of peaks in the range of a predetermined mass-to-charge ratio (m/z) and for selecting the predicted mass spectrum pattern which has a highest total ion intensity and comparing the predicted mass spectrum patterns having the highest total ion intensity with the measured mass spectrum to determine a nucleic acid base on the polymorphism point, and wherein the S(i) is compared with the selected predicted mass spectrum patterns.

15. A DNA analysis method for analyzing DNA polymorphism, comprising:

sampling by supplying a sample including a test DNA fragment for ionization intermittently at a predetermined time period;

generating plural kinds of multiply-charged ions of the test DNA fragment by ionization, where each of the multiply-charged ions has five or more charges;

performing a mass spectrometry on the multiply-charged ions formed by the ionization so as to measure a mass spectrum of the test DNA fragment;

performing the following treatment to obtain S(i) for the measured mass spectrum (I(i)) at an ordinal number "i", $$S(i) = I(i) - \sum_{n=1}^{m} w(n) I(i-n)$$

wherein m represents a predetermined natural number and w(n) represents a factor for the measured mass spectrum of the sample measured at n-th before the measurement of the sample which is measured at i-th;

predicting possible mass spectrum patterns in each of two cases, where one of the two cases is that the test DNA fragment is polymorphic and the other is that the test DNA fragment is not polymorphic, based on both an information about the number of each of four different nucleic acid bases that constitutes the test DNA fragment and an information about a polymorphism point, wherein the step of predicting includes predicting a mass-to-charge ratio (m/z; m is an ion mass, z is a number of electric charges) of each of the plural kinds of multiply-charged ions and a relative ion intensity corresponding to the mass-to-charge ratio (m/z) in each of the two cases; and comparing a plurality of the predicted mass spectrum patterns with the measured mass spectrum to determine a nucleic acid base on the polymorphism point, wherein the step of comparing includes selecting the predicted mass spectrum pattern such that a sum of a square root of a difference between a relative intensity of the measured mass spectrum having the S(i) and a relative intensity of the predicted mass spectrum pattern is smallest.

16. A DNA analysis method for analyzing DNA polymorphism, comprising the steps of:

predicting mass spectrum patterns when plural kinds of multiply-charged ions generated from a test DNA fragment, where each of the multiply-charged ions has five or more charges, in each of two cases, where one of the two cases is that the test DNA fragment is polymorphic and an other of the two cases is that the test DNA fragment is not polymorphic, based on information of a number of each of four different nucleic acid bases that constitute the test DNA fragment and information of a polymorphism point;

generating plural kinds of multiply-charged ions from a sample containing the test DNA fragment, where each of the multiply-charged lone has five or more charges;

performing a mass spectrometry on the multiply-charged ions to measure a mass spectrum pattern;

selecting a predicted mass spectrum pattern that is most closely analogous to the measured mass spectrum pattern by comparing a plurality of the predicted mass spectrum patterns the measured mass spectrum pattern.

17. The DNA analysis method according claim 16, wherein the selected predicted mass spectrum pattern that is most closely analogous to the measured mass spectrum pattern is selected from the predicted plural mass spectrum patterns by comparing a mass-to-charge (m/z; m is art ion mass, z is a number of electric charges) of a peak of the measured mass spectrum pattern with a mass-to-charge (m/z) of a peak of each of the plurality of the predicted mass spectrum patterns.

18. The DNA analysis method according claim 16, wherein the selected predicted mass spectrum pattern that is most closely analogous to the measured mass spectrum pattern is selected from the predicted plural mass spectrum pattern by comparing a mass-to-charge (m/z; m is an ion mass, z is a number of electric charges) and a distribution of an ion intensity of a peak of the measured mass spectrum pattern with a mass-to-charge (m/z) and a distribution of an ion intensity of a peak of each of the plurality of the predicted mass spectrum patterns.

19. The DNA analysis method according claim 16, wherein the steps of generating, performing and selecting are subsequently repeated, the measured mass spectrum pattern (I(i)) at an ordinal number "i" is subjected to the following treatment to obtain S(i), and then the S(i) is compared with each of the plurality of the predicted mass spectrum patterns, $$S(i) = I(i) - \sum_{n=1}^{m} w(n) I(i-n)$$

wherein m represents a predetermined natural number and w(n) represents a factor for the measured mass spectrum of the sample measured at n-th before the measurement of the sample which is measured at i-th.

20. The DNA analysis method according claim 16, wherein a mass spectrum pattern of a standard sample is measured when a maximum ion intensity of the measured mass spectrum pattern is smaller than a predetermined threshold.

* * * * *